United States Patent
Golway et al.

(10) Patent No.: US 9,910,935 B2
(45) Date of Patent: Mar. 6, 2018

(54) SYSTEM AND WORKSTATION FOR THE DESIGN, FABRICATION AND ASSEMBLY OF BIO-MATERIAL CONSTRUCTS

(71) Applicants: Michael Golway, Louisville, KY (US); Justin C. Palmer, Louisville, KY (US); Jeffrey Kyle Eli, Louisville, KY (US); Joshua D. Bartlett, Louisville, KY (US); Ellsworth H. Collins, Louisville, KY (US)

(72) Inventors: Michael Golway, Louisville, KY (US); Justin C. Palmer, Louisville, KY (US); Jeffrey Kyle Eli, Louisville, KY (US); Joshua D. Bartlett, Louisville, KY (US); Ellsworth H. Collins, Louisville, KY (US)

(73) Assignee: Advanced Solutions Life Sciences, LLC, Louisville, KY (US)

( * ) Notice: Subject to any disclaimer, the term of this patent is extended or adjusted under 35 U.S.C. 154(b) by 691 days.

(21) Appl. No.: 14/511,693

(22) Filed: Oct. 10, 2014

(65) Prior Publication Data
US 2015/0105891 A1 Apr. 16, 2015

Related U.S. Application Data

(60) Provisional application No. 61/889,856, filed on Oct. 11, 2013, provisional application No. 62/016,815, filed on Jun. 25, 2014.

(51) Int. Cl.
*A61F 2/38* (2006.01)
*A61F 2/30* (2006.01)
(Continued)

(52) U.S. Cl.
CPC .......... *G06F 17/50* (2013.01); *B25J 9/1679* (2013.01); *B29C 67/0055* (2013.01);
(Continued)

(58) Field of Classification Search
CPC ......... B33Y 30/00; B33Y 10/00; B33Y 50/02; B33Y 80/00; H01L 2924/00;
(Continued)

(56) References Cited

U.S. PATENT DOCUMENTS

| 6,143,293 A | 11/2000 | Weiss et al. |
| 6,986,739 B2 | 1/2006 | Warren et al. |

(Continued)

FOREIGN PATENT DOCUMENTS

| WO | 2011047040 | 4/2011 |
| WO | 2013049862 | 4/2013 |
| WO | 2014039429 | 3/2014 |

OTHER PUBLICATIONS

Christopher G. Geisler, A Thermosensitive and Photocrosslinkable Composite Polymer study for 3-D Soft Tissue Scaffold Printing, Jul. 2011, 183 pages.*

(Continued)

*Primary Examiner* — Thuy Dao
(74) *Attorney, Agent, or Firm* — Dinsmore & Shohl LLP

(57) ABSTRACT

A bioassembly system having a tissue/object modeling software component fully and seamlessly integrated with a robotic bioassembly workstation component for the computer-assisted design, fabrication and assembly of biological and non-biological constructs. The robotic bioassembly workstation includes a six-axis robot providing the capability for oblique-angle printing, printing by non-sequential planar layering, and printing on print substrates having variable surface topographies, enabling fabrication of more complex bio-constructs including tissues, organs and vascular trees.

21 Claims, 21 Drawing Sheets

(51) Int. Cl.
  *A61B 17/17* (2006.01)
  *G06F 17/50* (2006.01)
  *B29C 67/00* (2017.01)
  *C12M 3/00* (2006.01)
  *C12M 1/26* (2006.01)
  *B25J 9/16* (2006.01)
  *G05B 19/4099* (2006.01)
  *B29L 31/00* (2006.01)

(52) U.S. Cl.
  CPC ............ *C12M 21/08* (2013.01); *C12M 33/00* (2013.01); *G05B 19/4099* (2013.01); *G06F 17/5009* (2013.01); *B29L 2031/7532* (2013.01); *Y10S 901/02* (2013.01); *Y10S 901/30* (2013.01)

(58) Field of Classification Search
  CPC . H01L 2924/00014; H01L 2924/15144; H01L 2924/05155; A61F 2/30942; A61F 2002/30952; A61B 17/157; A61B 17/1764; C12N 5/0697
  See application file for complete search history.

(56) References Cited

U.S. PATENT DOCUMENTS

| | | | |
|---|---|---|---|
| 7,051,654 B2 | 5/2006 | Boland et al. | |
| 7,718,351 B2 | 5/2010 | Ying et al. | |
| 7,767,446 B2 | 8/2010 | Robbins et al. | |
| 7,855,074 B2* | 12/2010 | Warren ................ | C12N 5/0698 435/372 |
| 8,122,939 B2* | 2/2012 | Hochsmann ........... | B33Y 10/00 164/23 |
| 8,175,734 B2 | 5/2012 | Fogel et al. | |
| 8,241,905 B2 | 8/2012 | Forgacs et al. | |
| 8,636,938 B2* | 1/2014 | Bonassar ................ | A61L 27/36 101/491 |
| 8,639,484 B2 | 1/2014 | Sun et al. | |
| 8,790,408 B2* | 7/2014 | Marotta ................ | A61B 19/50 623/17.19 |
| 9,149,952 B2* | 10/2015 | Murphy .................... | B41J 3/407 |
| 9,326,834 B2* | 5/2016 | Morales ................ | A61C 13/01 |
| 9,499,779 B2* | 11/2016 | Murphy ................ | C12M 29/00 |
| 9,636,229 B2* | 5/2017 | Lang ....................... | A61F 2/389 |
| 2005/0005707 A1* | 1/2005 | Li .......................... | B82Y 10/00 73/832 |
| 2005/0074088 A1* | 4/2005 | Ichihara ............... | G01N 23/046 378/58 |
| 2006/0195179 A1 | 8/2006 | Sun et al. | |
| 2009/0208466 A1 | 8/2009 | Yoo et al. | |
| 2009/0208577 A1 | 8/2009 | Xu et al. | |
| 2009/0239302 A1 | 9/2009 | Decher et al. | |
| 2010/0075293 A1 | 3/2010 | Chang et al. | |
| 2011/0169193 A1 | 7/2011 | Bonassar et al. | |
| 2011/0177590 A1* | 7/2011 | Clyne ..................... | A61L 27/38 435/325 |
| 2011/0212501 A1* | 9/2011 | Yoo ........................ | A61L 27/54 435/174 |
| 2011/0262640 A1* | 10/2011 | Dosier .................... | C04B 24/14 427/215 |
| 2012/0116568 A1 | 5/2012 | Murphy et al. | |
| 2012/0201890 A1 | 8/2012 | Williams et al. | |
| 2013/0017564 A1* | 1/2013 | Guillemot ............. | B01L 3/0268 435/8 |
| 2013/0158651 A1 | 6/2013 | Hollister et al. | |
| 2013/0164339 A1 | 6/2013 | Murphy et al. | |
| 2013/0170171 A1* | 7/2013 | Wicker ................ | H01L 21/4846 361/809 |
| 2013/0190210 A1 | 7/2013 | Murphy et al. | |
| 2013/0345794 A1 | 12/2013 | Khatiwala et al. | |
| 2014/0012407 A1 | 1/2014 | Murphy et al. | |
| 2014/0230965 A1* | 8/2014 | Waterman ................ | B27H 5/00 144/330 |

OTHER PUBLICATIONS

S. Takeuchi, Cell-laden hydrogel beads, fibers and plates for 3D tissue construction, 2013, 4 pages.*
V. Mironov, Organ Printing: How to print a human organ, Jun. 2010, 97 pages.*
International Search Report and Written Opinion for corresponding PCT Application No. PCT/US2014/060042 dated Jan. 29, 2015.
Q&A with Keith Murphy, CEO of Organovo Holdings Inc. (ONVO) posted online by Gary Anderson at http://www.engineering.com/Library/ArticlesPage/tabid/85/ArticleID/6534/QA-with-Keith-Murphy-CEO-of-Organovo-Holdings-Inc-ONVO.aspx, Oct. 2013.

* cited by examiner 8  13  11  12  14

A

B

A

B

A

B

C

A

B

C

A

B

A

B

SYSTEM AND WORKSTATION FOR THE DESIGN, FABRICATION AND ASSEMBLY OF BIO-MATERIAL CONSTRUCTS

PRIORITY CLAIM

This application claims priority to U.S. Provisional Application No. 61/889,856, filed on Oct. 11, 2013 and U.S. Provisional No. 62/016,815 filed on Jun. 25, 2014, the entire disclosures of which are incorporated herein by this reference.

TECHNICAL FIELD

The disclosure relates to computer-assisted design of tissue structure models, robotic fabrication and bioassembly, and a workstation for the design, fabrication and assembly of complex biological constructs. The bioassembly system enables users to design/model, fabricate and/or analyze complex tissue structures facilitated by novel Tissue Structure Information Modeling (TSIM) software.

BACKGROUND

Tissue engineering via 3-D biomaterial dispenser-based precision deposition is a fast-evolving technology that has gone from provocative science fiction to the realization of 3-D "bioprinted" functional organ slivers in just a little over a decade. For simplicity, as used herein "bio-printing" refers broadly to any biomaterial dispensing technology utilizing three-dimensional, precise deposition of biomaterials via methodology that is compatible with an automated, computer-aided, three-dimensional prototyping device (a bioprinter). Computer assisted design (CAD)-facilitated 3-D bioprinters are now available as retail products, and companies engaged in commercializing bioprinters and bioprinted products are publicly traded on the New York Stock Exchange. The rapid growth in the 3-D tissue engineering industry is in large part due to a demand for transplantable organs and organ repair tissues that is increasing at a faster rate than the supply. Hence, the prospect for urgent timeframe, large volume fabrication of synthetic biological constructs, including functional tissues and organs, has widespread appeal and has achieved significant private and government resource commitment.

Bioprinting and bioprinters have advanced significantly in recent years; however a stand-alone bioprinter still has very little useful functionality. End-users must often develop their own software and set up suitable workstations—tasks requiring expertise in computer-assisted-design, electronics and related materials engineering, as well as in the relevant biological science. Hence, without resources for and access to a team of experts, designing and bioprinting biological constructs such as tissues and organs remains the province of large well-funded research organizations and entities.

Conventional tissue engineering systems based on bioprinting technologies also typically require large work spaces because design, printing and assembly are typically effectuated on different platforms.

State-of-the-art bioprinters offer a wide variety of functionality, in particular at the dispensing end, where consumers may choose from single to multi nozzle print heads and from a wide range of biomaterial dispensing mechanisms. Contact-based deposition techniques such as soft lithography and non-contact based deposition techniques such as pressure-actuated ink jetting and laser-guided direct writing, have all been exploited in bioprinter design. Most bioprinters, however, rely on movement of the print head along three axes, which achieves precise deposition in two dimensional planar coordinates, but which limits building complex tissue and organ constructs to a layer-by-layer protocol, resulting in build support complications and other build challenges in multi-tissue constructs.

There remains a need for a technologically comprehensive tissue design and fabrication workstation fully integrated with tissue modeling and operational software to provide user-friendly functionality for CAD-assisted tissue engineering, and a need for workstation designs which achieve modeling, fabrication and assembly in a more compact work space. Further, there remains a need for bioprinter designs that provide greater flexibility in build protocols.

SUMMARY

Accordingly, embodiments of the invention provide an intuitive, user-friendly tissue structure design and fabrication system, referred to herein as a bioassembly system, facilitated by software that seamlessly integrates the design and fabrication modalities. The bioassembly system comprises two major components: (i) software for "Tissue Structure Information Modeling" (TSIM) and (ii) hardware for staging, printing and assembling bio-constructs, referred to as the "Robotic Bioassembly Workstation" (RBW). The RBW provides a compact, and in some embodiments, a mobile workspace, in which print/fabrication and assembly may take place on the same platform. The robotic aspect is capable of switching between different modalities including staging, printing and assembling. Greater build versatility is achieved by utilization of a robotic arm capable of movement along at least six different axes, thus providing capability of dispensing biomaterial by non-sequential planar layering and by providing capability of dispensing on 3-D surfaces of variable surface topographies.

One embodiment of the invention provides a bioassembly system comprising a tissue modeling component and a robotic bioassembly workstation component. The tissue modeling component comprises a user interface, at least one suite of tools for performing an object operation selected from the operation categories of creating, editing, modeling, transforming, image property modulating, sketching, print supporting, simulating, material testing and combinations thereof, a material database, and software executable by a machine to facilitate a method for designing a volumetric model of a biological construct at the user interface.

The tissue modeling component is operationally linked to a robotic bioassembly workstation component and the method comprises: adding at least one object to an object modeling environment at the TSIM-user interface, wherein adding comprises selecting, creating, importing and combinations thereof, and further wherein each added object may be associated with an object list comprising material and/or environmental build parameters; performing one or more operations on the one or more objects in the modeling environment to render a desired volumetric model; transmitting the rendered volumetric model to the robotic bioassembly workstation with a print and/or assembly command; and printing and/or assembling the modeled object as a bioconstruct.

According to some embodiments, a simulation or materials test may be conducted prior to effectuating the printing/fabricating command.

Another embodiment is directed to a robotic biomaterial dispensing apparatus comprising a robotic arm and a robotic arm end effector. The end effector is configured to grip and secure a dispensing syringe and the robotic arm provides movement of the syringe along at least six axes.

Other embodiments are directed to the bio-constructs designed, fabricated and assembled utilizing the bioassembly system and according to the inventive methods.

These and other embodiments will be more clearly understood and appreciated by reference to the figures and detailed disclosure set forth below.

DETAILED DESCRIPTION

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

As used in this specification and the appended claims, the singular forms "a," "an," and "the" include plural references unless the context clearly dictates otherwise. Any reference to "or" herein is intended to encompass "and/or" unless otherwise stated.

As used herein, "biomaterial" means a liquid, semi-solid, or solid composition comprising a plurality of cells, cell solutions, cell aggregates, multicellular forms or tissues, and in all cases may include support material such as gels, hydrogels, alginate or non-cellular materials that provide specific biomechanical properties that enable biomaterial printing.

As used herein, "cartridge" means any object that is capable of receiving (and holding) a biomaterial and/or a support material and used interchangeably with "syringe barrel."

A bioassembly system comprising a tissue modeling component and a robotic bioassembly workstation component is disclosed and detailed herein. The bioassembly system is an integrated solution for tissue structure modeling, fabrication and assembly comprising a software component referred to herein as Tissue Structure Information Modeling or TSIM, and a hardware component referred to herein as a Robotics BioAssembly Workstation, or RBW. TSIM permits clinicians and scientists to design, visualize, simulate, and analyze three dimensional (3-D) computer models of complex biological constructs, including tissue structures created from traditional sources of medical imaging technology. TSIM provides a computer-assisted-design (CAD) platform that is particularly suited for end-users without specific expertise in conventional CAD software.

Figure 4:
FIG. 4. 4A depicts an exemplary object modeling environment at the TSIM user interface; 4B depicts an exemplary TSIM operations tool panel in the object modeling environment.
Figure 4:

Generally, TSIM comprises software and a user interface comprising an object modeling environment. TSIM comprises several suites of tools for performing one or more object operations. Object modeling tools include but are not limited to tool suites for creating, editing, modeling, transforming, image property modulating, sketching, print supporting, simulating, material testing and combinations thereof. In some embodiments a materials database is provided, and in specific embodiments objects stored in an object list are associated with specific materials and material use parameters. FIG. 4B depicts an exemplary object list displayed in association with a selected object. The TSIM software is executable by a machine to facilitate methods for designing volumetric models of biological constructs at the TSIM-user interface in what is referred to herein as an object modeling environment.

TSIM is operationally linked to the robotic bioassembly workstation component such that once a user has completed a modeling task, the user may send a print command (see FIG. 21 for an exemplary print command screen at the TSIM-UI) to the RBW to initiate printing/fabrication/assembly.

For purposes of the following disclosure, reference to a particular Example and/or Figure is made to provide additional illustration/detail and explanation of the functionality/operation.

When integrated in a work flow, the bioassembly system designs, fabricates and assembles complex three-dimensional biomaterial constructs, including but not limited to cellular systems, tissues, organs, and implantable medical devices and jigs. The RBW aspect comprises a material storage unit including a syringe holder and multiple cartridges (syringe barrels) each with a set of syringes, and a robotic arm component with an end effector capable of gripping, holding, and connecting specialized syringe, and a dispenser. According to specific embodiments the bioassembly system ultimately achieves CAD-based extrusion dispensing of biomaterials. Suitable materials include but are not limited to biomaterials such as cells, biosupport materials such as gels, and non-biological materials, for example in the design and fabrication of implantable jigs. Combinations of biomaterials, biosupport materials and non-biological materials may be utilized in the same fabrication.

As used herein, "dispensing of biomaterials" may be effectuated by any bioprinting technique including but not limited to inkjet, extrusion/microextrusion, and laser-assisted printing. Thermal inkjet printers electrically heat the printhead to produce air-pressure pulses that force droplets from the nozzle, while acoustic printers use pulses formed by piezoelectric or ultrasound pressure. Extrusion printers typically rely on pneumatic or mechanical (piston or screw) dispensing mechanisms to extrude continuous beads or filaments of biomaterial (or non-biomaterial). Laser-assisted printers use lasers focused on an absorbing substrate to generate pressures that propel cell-containing materials onto the substrate. According to preferred embodiments, the robotically controlled bioprinting of the RBW comprises extrusion dispensing onto a substrate.

Figure 5:
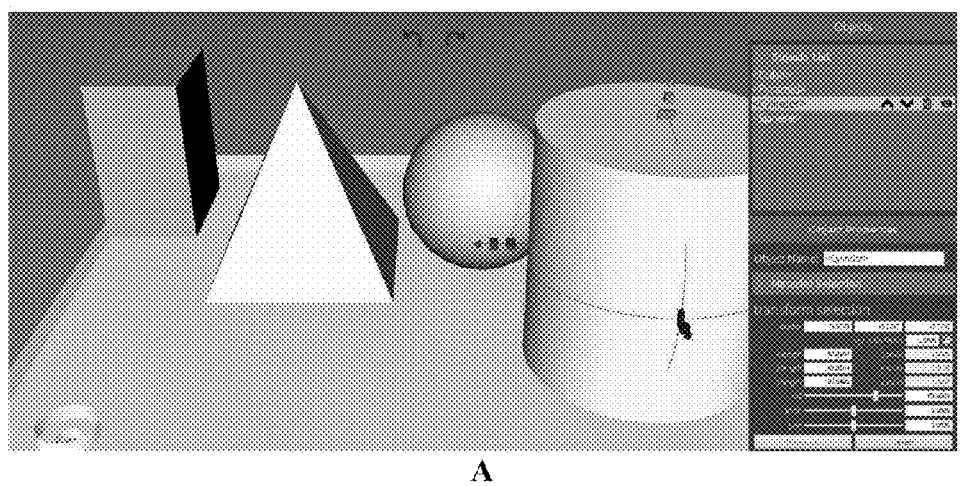
FIG. 5. 5A depicts an exemplary volumetric object menu showing display of an object list once an object is selected; 5B depicts an exemplary modeling environment displaying an object list materials selection.
Figure 5:
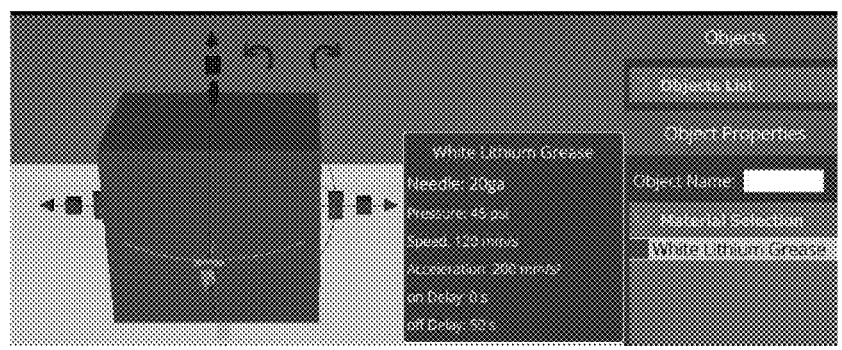
Figure 6:
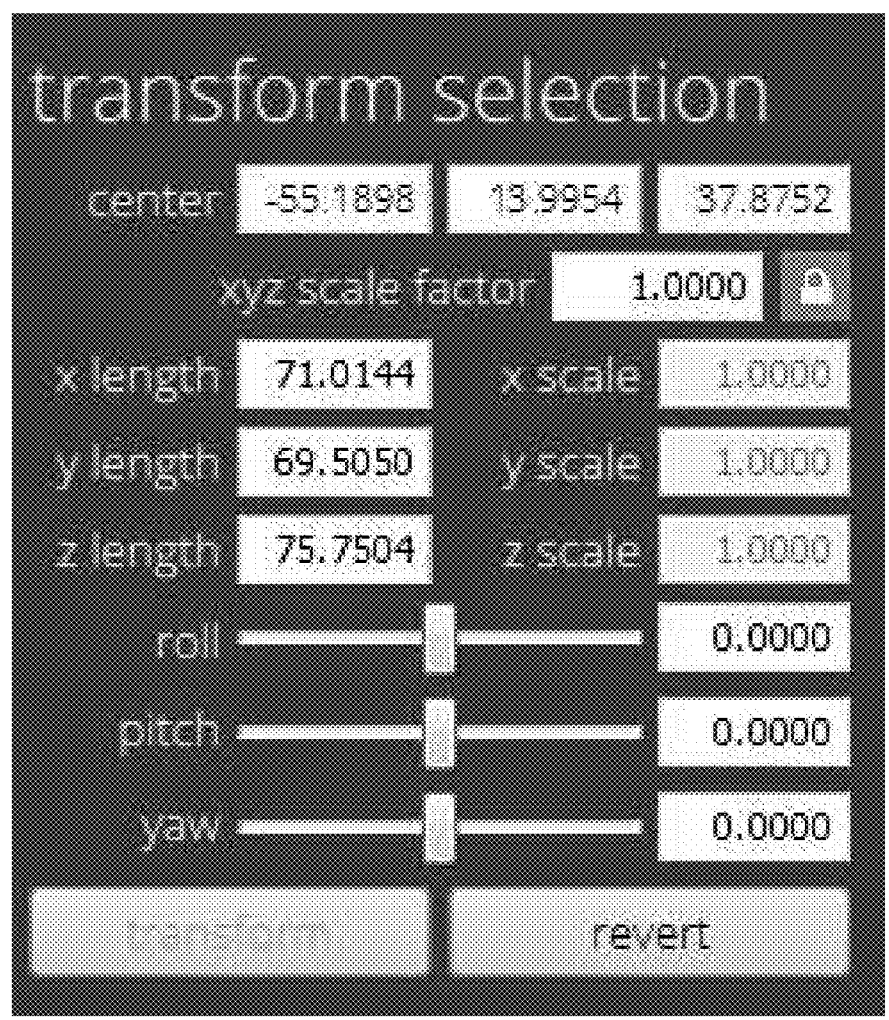
FIG. 6. Depicts a specific modeling environment screen illustrating an exemplary transformation operation panel.

According to particular embodiments, a user at the TSIM-UI may "add" one or more objects to an object modeling environment. An exemplary TSIM-UI screen showing an object modeling environment along with an operations tool panel is set forth in FIGS. 4A and 4B, respectively. Adding may be effectuated by different functional capabilities. An object may be added by selecting from a panel linked to a stored database of pre-existing objects (FIG. 5A). In specific embodiments the panel comprises one or more of a cube, a cylinder, a sphere and a pyramid as basic shapes. The shapes may be edited and/or transformed and stored as new objects on the panel for future applications. In specific embodiments, other objects may be added to the stored panel and it is contemplated that a user will add/create and import objects to yield a customized menu/panel of stored objects from which to select for addition to the object modeling environment.

Figure 7:
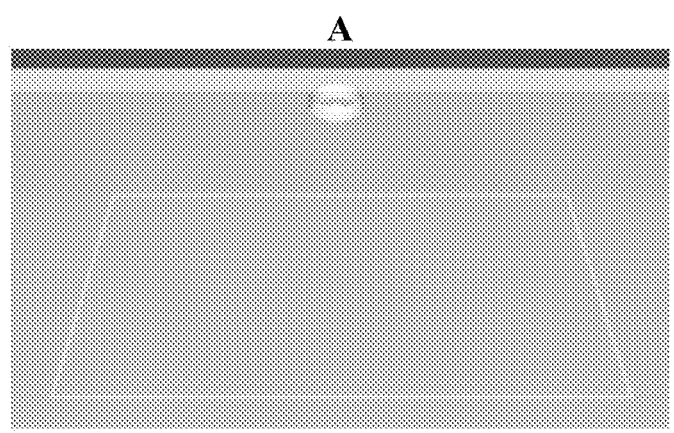
FIG. 7. Depicts specific modeling environment screens illustrating creating a box; 7A depicts setting the base of a box; 7B depicts setting the height of the box; 7C depicts a final volumetric box.
Figure 7:
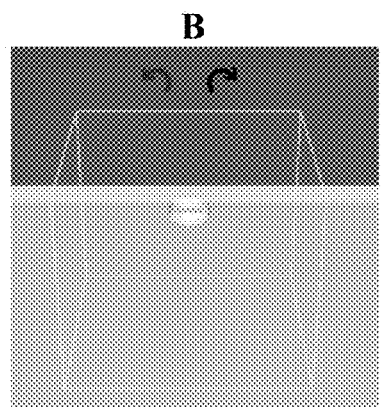
Figure 7:
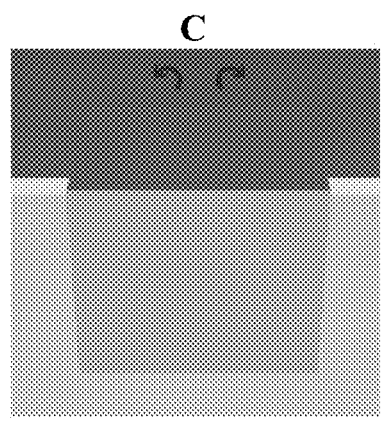
Figure 8:
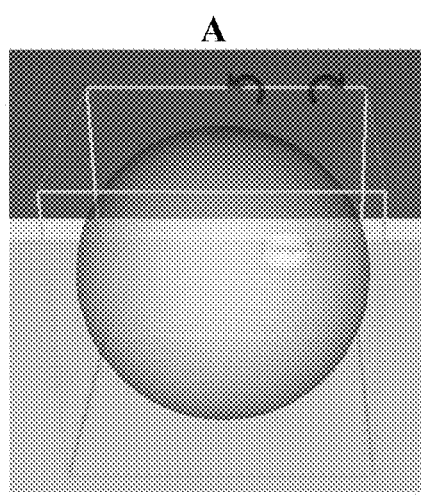
FIG. 8. Depicts specific modeling environment screens illustrating creating a sphere; 8A shows setting the diameter of a sphere; 8B shows a final volumetric sphere.
Figure 8:
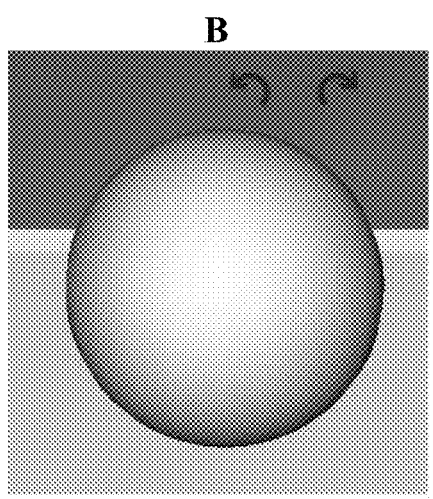

In other embodiments, objects may be created directly in the object modeling environment. As illustrated in Example 1, by using the basic cube/box (FIG. 7), sphere (FIG. 8), cylinder (FIG. 9) and/or pyramid (FIG. 10) operations, a user may create basic shapes/objects and then manipulate, modify, edit, transform, add, intersect, e.g. the objects to derive a number of novel volumetric objects. The term "volumetric" is used herein to mean solid, three-dimensional forms.

Figure 17:
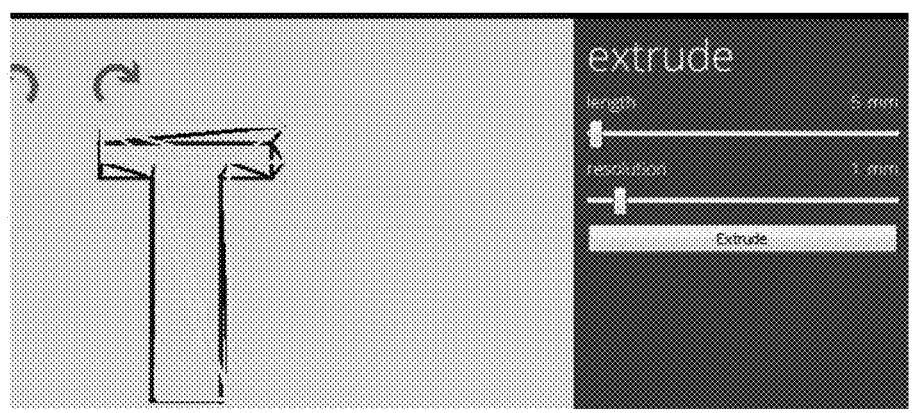
FIG. 17. Depicts a specific modeling environment screen illustrating an extrusion operation to convert a sketch into a volumetric model.

In specific embodiments, an object may be created in the modeling environment by sketching and then performing operations on the sketch. Basic sketching functionality is illustrated in Example 5. A user may also sketch a 2-dimensional (2-D) bounded construct and perform an extrude operation (Example 6 and FIG. 17) in at least one direction to form a novel model volumetric object. A user may sketch bounded constructs on multiple planes in xyz space and connect particular boundaries to form novel objects, and a user may loft one or more of the contours of any object or sketch to varying degrees to further create new volumetric objects (Example 7 and FIG. 18).

Figure 19:
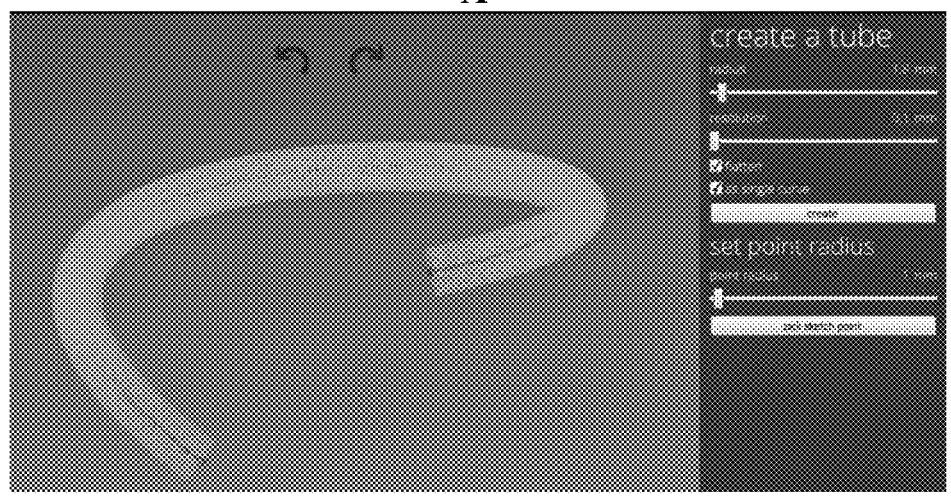
FIG. 19. Depicts a specific modeling environment screen illustrating the "create a tube" operation; 19A depicts selecting a radius for an unbounded sketch in the modeling environment; and 19B click the "create a tube" operation icon to form a volumetric tube.
Figure 19:
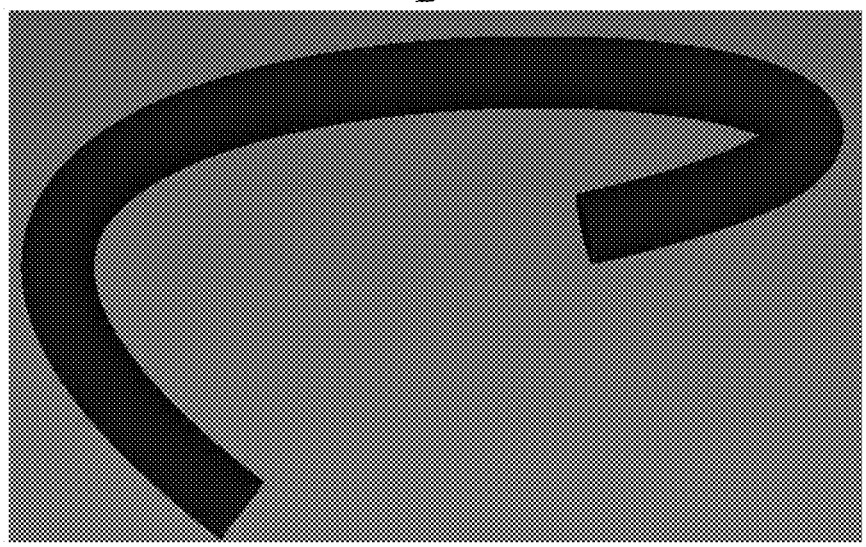
Figure 20:
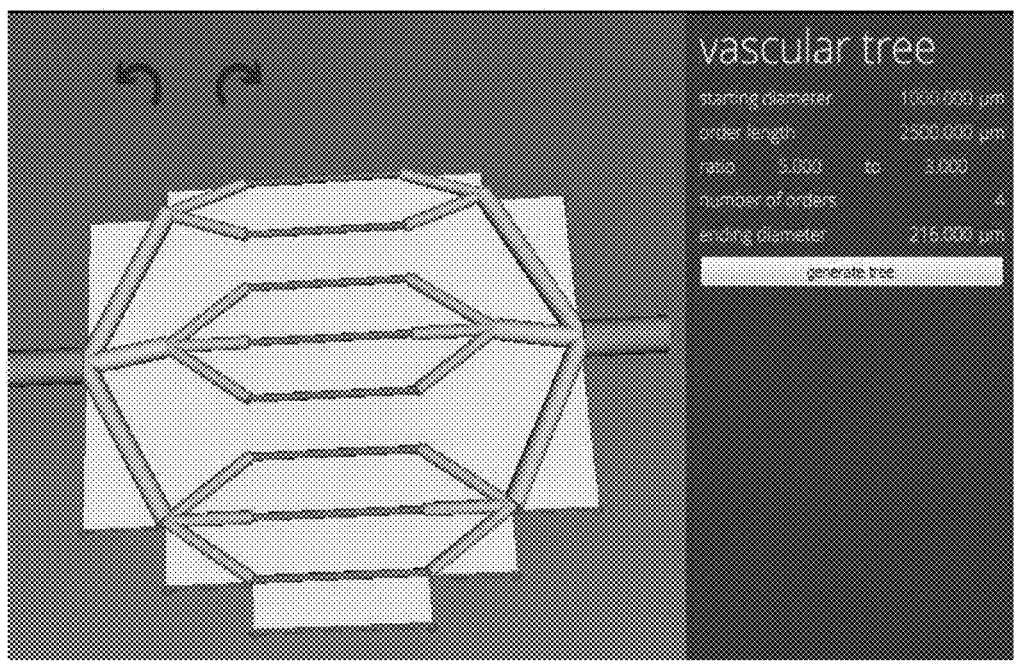
FIG. 20. Depicts a specific modeling environment screen for creation of a vascular tree and an exemplary vascular tree.

One specific embodiment exemplified in FIG. 19 and Example 9 provides a tube operation whereby a user creates a curve in two or three-dimensional space, selects a radius, and performs a tube operation to yield a tube. Tubes, like all other object models, may be edited, transformed, modified, combined with other objects, and the like. According to another specific embodiment, a user may create a vascular tree model by performing a vascular tree operation by setting a parameter profile as exemplified in Table 2 (FIG. 20 and Example 8). Non-limiting examples of input parameters for formation of a model vascular tree comprise starting diameter, order length, ratio, number of orders, and ending diameter. A vascular tree may be fabricated on a print substrate having variable surface topographies to provide a highly intricate and embedded vascular construct for fabrication into more complex bio-constructs such as tissues and organs.

According to other embodiments, an object may be added to the modeling environment by importing an object from an external file. Users may open existing model files created in external programs and import them directly through TSIM. Exemplary importable file formats include STL, NIfTI and DICOM. Specific embodiments illustrating importing in each of these file formats are set forth in Example 3. External files derived from any medical imaging technology may be imported, although in certain specific embodiments, adaptation or conversion of the file may be necessary. Non-limiting examples of medical imaging technology from which importable images may be derived include magnetic resonance imaging, X-ray radiography, medical ultrasound, endoscopy, elastography, tactile imaging, thermography, medical photography and positron emission tomography.

Data generated from medical imaging technology is imported to TSIM, analyzed, and used to generate 3-D models or model scaffolds and/or tissue constructs customized to be patient-specific. In certain embodiments, tissues, organs, medical devices and medical jigs may be modeled and fabricated clinically in situ based on specific needs of a patient.

The bioassembly system includes a TSIM user interface which permits user input to guide the model-generation process. 3-D models may be combined with pre-loaded "tissue engineering recipes" containing necessary material and/or cell types, assembly parameters, and an assembly instruction sequences. TSIM may also include functionality for simulation testing. The RBW may further comprise an environmental sensing system including visualization capability, and in some embodiments is capable of providing verification feedback to a user during the assembly process. In some cases assembly may include integration of biological with non-biological constructs.

The RBW allows users to sub-assemble and assemble complex tissue structures, and to assemble tissue constructs into higher order biological constructs including organs. According to some embodiments, material cartridges/barrels are loaded manually into the RBW by the user, and are placed in the syringe barrel holders. The RBW user-interface may assist the user throughout the process of loading the material cartridges. In specific embodiments the RBW comprises a plurality of syringe barrels containing different materials that can be changed automatically or manually. Other than space constraints, there is no limit to the number of barrels which may be loaded into the RBW for specific uses. In very specific embodiments the robotic workstation comprises between 2 and 12 syringe barrels. In even more specific embodiments the robotic workstation comprises 12 syringe barrels.

The RBW is capable of conducting a change in tooling using an interlocking mechanism of the barrel adapter and an interchangeable component. A material storage system stores the interchangeable components in a fixed orientation when not in use. A gripper temporarily immobilizes the interchangeable component relative to the gripper, while a robotic joint (J6) performs a twisting motion of the barrel adapter to lock or unlock the mechanism. When in the locked position, the tool can be used as needed.

To load material cartridges for printing, the robot moves to the appropriate storage rack location for pickup. After aligning with the syringe position, the robot moves the adapter head of the end effector directly onto the top of the syringe barrel. The robot gripper engages and raises the syringe barrel out of the holder. Next, the robot's J6 motor locks the syringe barrel into the adapter head to prepare for assembly, after which the gripper disengages and the robot returns into the home position.

Once the appropriate material cartridge has been prepared, loaded and positioned for printing, the material is dispensed onto the RBW print stage based on the print/assembly path specified from TSIM.

Depending on the materials needed to produce a complex tissue structure, the robot swaps material cartridges as needed. In order to periodically clean the nozzles and ensure quality prints, the robot may migrate over to a cleaning surface and clean the needle tip. A dispensing syringe may be fitted with needles of varying sizes and lengths, according to particular project demands.

The RBW is an integrated workstation comprised of a multi-axis robot and controller, integrated cell and material cartridge containment and dispensing aspect, an environmental control aspect and intelligent visual aspect, configured to provide a compact convenient table-top workstation for bioconstruct assembly needs.

TSIM and the RBW operate together to provide a comprehensive integrated software and hardware technology platform including medical imaging analysis, biological construct modeling, physical simulation, fabrication and assembly.

According to one exemplary embodiment, TSIM is used to effectuate importing patient-specific tissue structures and combining them into a 3-D biological computer models with corresponding Tissue Engineering Recipes (e.g., a heart valve, ear lobe, etc.) that contain bill of material and/or cell types, assembly specifications (e.g., environmental control) and assembly sequence (e.g., apply cell type 1 and then integrate a vascular network). In this manner, a properly engineered tissue structure can be applied to specific patient biometrics to achieve a solution that is viable and practical for medical replacement/implantation utilities or, for example, laboratory testing of medicines and medical devices.

TSIM includes the capability to simulate a wide range of real world variables to analyze resulting outcomes. Simulation modules include, but are not limited to, material viscosity and assembled shape deformation, tissue structure analysis, vascular fluid dynamics, and the like.

The RBW is integrated seamlessly with TSIM to allow a user to obtain a fully assembled bioconstruct or physical tissue structure of the 3-D models developed within the software program. The multi-axis robot receives assembly steps and information from the TSIM software that includes material types and appropriate environmental conditions (e.g., temperature, UV light, humidity, etc.). The robotic visual system provides real time feedback to both the user and TSIM to intelligently detect assembly quality and for verification of design specifications.

In some embodiments, an automated materials/configuration testing protocol is provided prior to fabrication. In certain embodiments the user configures each syringe barrel or cartridge to provide unique dispensing characteristics for each object or object feature printed. Prior to actual fabrication, test applications may be effectuated whereby a configuration may be adapted through observation or automatic indication via feedback to TSIM of the quality of printing. A test pattern may include, for example, an appropriate two-dimensional or three-dimensional pattern to test and tune the print quality such as start/stop/delay, line width, speed, pressure, and acceleration. In specific embodiments a user is able to stop a test print at any time, for example upon real-time observation or indication of an error. Once fine-tuned, final configurations may be saved and transferred into TSIM for future applications.

The RBW comprises a closed-loop cartridge dispensing system. "Cartridges" may be any material containment and dispensing article and may be custom-engineered or purchased and contain specific material including specific cell types, biological or non-biological structural support material, and other materials as appropriate/desired for particular assembly applications. A cartridge may also be referred to herein as a syringe barrel. The RBW permits loading or retrieval of a specific material/cell cartridge that corresponds to what is specified in the TSIM-generated 3-D modeling protocol. When a TSIM 3-D model is ready to be "printed," the user loads the cartridges containing the material/cell types specified in the model into the robotic workstation.

According to specific embodiments user-error is substantially controlled through the workstation visualization and sensing system. For example, the workstation robot may scan a bar code affixed on the cartridge to verify and validate vital information such as material type, lot number, date, temperature etc. Laser displacement sensors may be used to ensure that syringe barrels are properly seated and secured in the material storage unit.

Once verification has been completed, the robot employs a specially designed end effector to grip and secure the cartridge and move to the print/assembly stage within the workstation. End effectors may comprise the capability to load multiple cartridges at one time to enhance assembly time. The workstation robot then executes the assembly instructions and steps that it receives from TSIM.

Biological models are created with TSIM using different workflows. According to a first workflow, users can choose to build a model by importing medical images and then performing operations on the model to shape and refine the final 3-D model to be used for printing. A model may be refined further by defining objects using the acquired 2-D image set in an Advanced User 2-D Image Editor module.

According to a second workflow, users create models using basic shapes. In one aspect of the second workflow, a basic set of geometric shapes is available to users (e.g., cube, cylinder, sphere, pyramid), all of which can be selected and placed directly into the object modeling environment and combined, stretched and deformed to meet specific application needs. In addition, manipulation commands such as *Difference, *Intersect, and *Union are available for the user to create a desired shape.

Once created, users may run simulations on a model to determine whether or not the constructed output will be structurally sound after printing. After simulations confirm the structural integrity of a printed structure, the user selects the Print command. Once activated, the Print command sends information to the RBW for object fabrication and assembly.

In very specific embodiments, TSIM utilizes Insight Toolkit (ITK), a C++ library, in order to perform data registration and segmentation. In certain embodiments, data used by TSIM may be found in digitally sampled representations of tissue (i.e., images acquired from medical instrumentation such as CT and MRI machines). Segmentation is the process of identifying and classifying the data found in digitally sampled representations. Registration is the task of aligning or developing correspondences between data sets. For example, a CT scan can be aligned with an MRI scan in order to combine the information contained in both representations. ITK will allow TSIM to consume medical data and then combine different data sets to provide the most complete representation of a tissue structure to the user.

(ITK was originally developed by the US National Library of Medicine. A consortium was put together to manage the project, called the Insight Software Consortium. ITK is licensed under the Apache 2.0 license and the ITK Press Kit may be found at the following link: http://www.itk.org/ITK/project/press_kit.html.)

Data Visualization and Modeling

In specific embodiments, TSIM utilizes Visualization Toolkit (VTK) for image processing, modeling, and volume rendering. This toolkit easily interfaces with ITK, allowing images analyzed using ITK to be modeled in 3-D. VTK, like ITK, is a C++ library. Thus, users are able to import images into TSIM (powered by ITK), edit imported images, and visualize constructed 3-D models of tissue structure(s) (powered by VTK). (VTK is licensed under the BSD (3-Clause) License, which allows the commercial use, modification, distribution, and sublicensing of the code, and the VTK press kit is located at http://www.vtk.org/VTK/project/press_kit.html.)

Medical Image File Format Support.

In very specific embodiments, TSIM supports a variety of standard imaging formats including DICOM, NIfTI, and the FLUOVIEW FV1000 Version 2 OIF file format for importing medical imaging data and associated metadata. The DICOM file format is the Digital Imaging and Communications in Medicine standard for handling, storing, printing, and transmitting information in medical imaging. It includes a file format definition with a set of tags that contain information such as pixel format, modality, and patient information. Images stored in the DICOM format can be stored as a series of DICOM files in which each contains a single image plane. The NIfTI file format stems from the Neuroimaging Informatics Technology Initiative, a working group sponsored by the National Institute of Health. The file includes a header and data. The header includes such information as the pixel format and depth, pixel spacing, and X, Y, Z, T image dimensions. If multiple image planes are saved, NIfTI files store the data as one all-encompassing file. The FLUOVIEW FV1000 Version 2 OIF file format is a specific confocal microscopy format that contains header information within the OIF (Original Imaging Format) file and within the individual PTY files. This format also saves Tagged Image File Format (TIFF) image files and the PTY files reference the TIFF images and contain the pixel data and dimensioning to be used when reconstructing the image stack. This file format is capable of storing multiple channels of data. In certain embodiments TSIM uses the first channel.

Imported Image Quality.

TSIM provides users the option to import medical imaging data at full or lower resolution. The user is presented with a quality sliding bar, that when adjusted either increases or decreases the resolution of a preview image. For comparison, the original full quality image may also be previewed. Below the preview images, a thumbnail slider may be available so that the user can view the effects of the quality changes on multiple portions of the image set. The added value of this functionality is that it will free up RAM for additional computing power that can be used for other TSIM operations.

3-D Model Editor—Loaded Volume

After importing an image set, a set of preview images is presented to the user, each of which has a different preset filter applied. The user selects the most desirable image according to the needs of the application. The user will then be presented with another set of preview images that have the first filter they selected applied but now with an additional filter applied. The user will then pick the most desirable image, and this process will continue for multiple, for example 3, total iterations. After the process is over, a 3-D model is generated using the preset filters indirectly chosen by the user.

This 3-D model can then be edited to show the data that the user is most interested in capturing. Initial 3-D model editing may be done using TSIM tools. Tools available in TSIM to the user for creating, editing and transforming objects in the object modeling environment are set forth below.

Spline Tool: This tool will allow the user to define splines within the 3-D model. These splines may be used as reference lines. A user draws splines to define the boundary of objects within the 3-D model and these are used in the generation of the final solid 3-D model. If the model has been constructed using imaging data, while utilizing the spline tool the user will be able to use the mouse scroll wheel to scroll up and down the model through the 2-D image stack as can be seen in the heart model of Figures x. The user is able to scroll to a desired image in the stack and snap their splines to that image plane in order to better define tissue structures.

Region of Interest Tool: This tool can be used by the user to define a region of interest within the 3-D model by creating a closed loop (ends are connected) free form spline around a desired portion of the 3-D model. The user must orient the model into the desired view before making the spline. After the region has been defined by the user, the spline will extend infinitely in the z direction. The 3-D model will then update and exclude all data that wasn't included in the region of interest (Figure x).

Eraser Tool: This tool turns the user's mouse cursor into an eraser in the shape of a sphere within the 3-D rendering window. After selecting the tool, the user can erase image data by clicking and holding the left mouse button. Additionally, the eraser size can be changed to facilitate the erasure of smaller or larger features. The user can then switch the tool off and the 3-D model will update automatically.

Cube Tool: This tool permits users to create cubes in model space. Once selected, a standard cube may be generated in the model space that can be resized and moved using manipulators located on the cube. In addition, input will be available for coordinate positioning, for example, X, Y, and Z positioning, and for scale of the object.

Cylinder Tool: This tool allows users to create cylinders in model space. Once selected, a standard cylinder will be generated in the model space that can be resized and moved using manipulators located on the cylinder. In addition, input will be available for coordinate positioning, for example, X, Y, and Z positioning, and for scale of the object.

Sphere Tool: This tool allows users to create spheres in model space. Once selected, a standard sphere will be generated in the model space that can be resized and moved using manipulators located on the sphere. In addition, input will be available for coordinate positioning, for example, X, Y, and Z positioning, and for scale of the object.

Exemplary 3-D Modeling Tools

Pan—This tool is used to shift the viewing angle of a modeling space left, right, up or down.

Rotate—This tool is used to rotate the 3D model about, for example, a 3-dimensional axes (X, Y, Z).

Zoom—This tool is used to magnify or de-magnify a model as it is presented on the computer screen.

Intersection—This tool is used to define a region boundary based on the intersection of two splines/objects.

Difference—This tool is used to define a region boundary based on the subtraction of an actively selected object from an inactive object.

Figure 9:
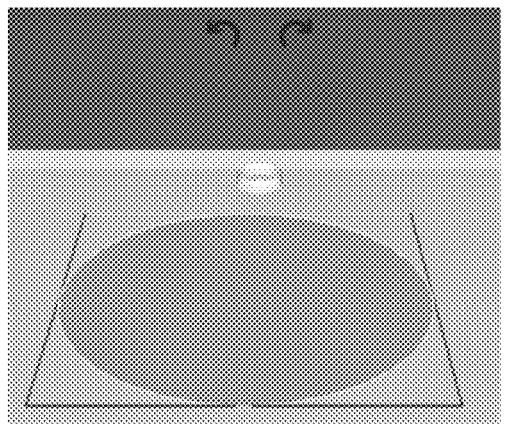
FIG. 9. Depicts specific modeling environment screens illustrating creating a cylinder; 9A shows setting the base of a cylinder; 9B shows setting the height of the cylinder; 9C shows a final volumetric cylinder.
Figure 9:
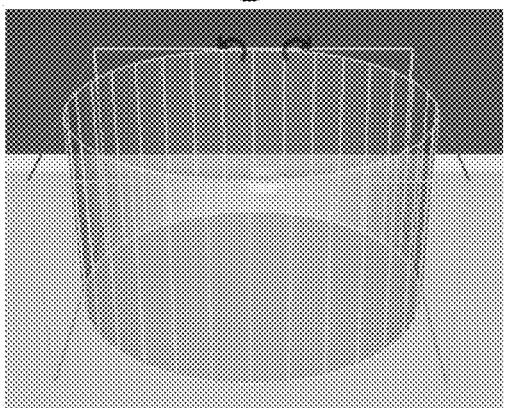
Figure 9:
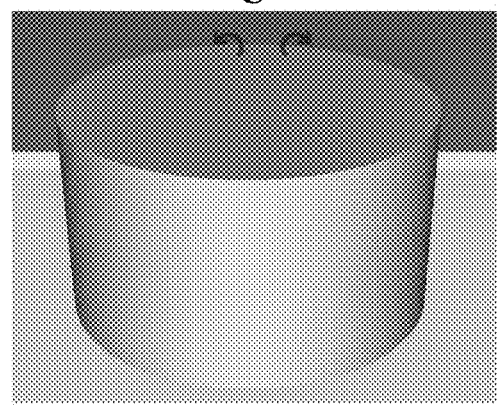
Figure 10:
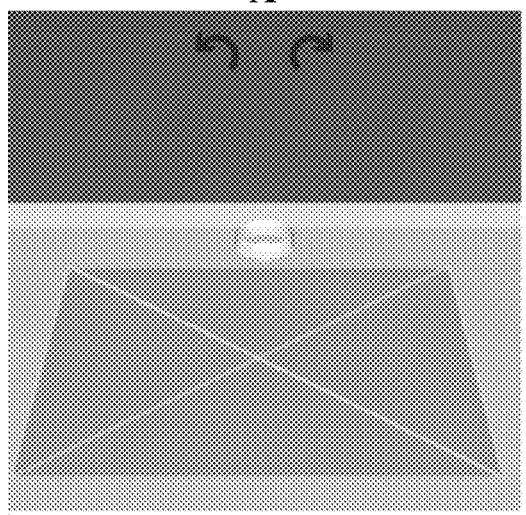
FIG. 10. Depicts specific modeling environment screens illustrating creating a pyramid; 10A shows setting the base of a pyramid; 10B shows setting a height of the pyramid; 10C shows a final volumetric pyramid.
Figure 10:
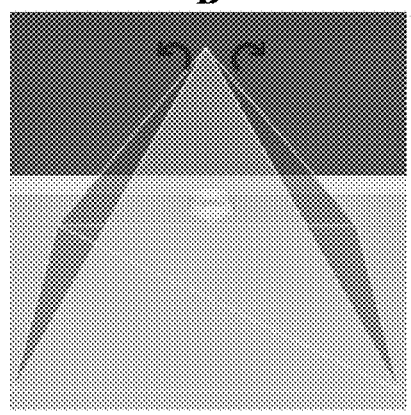
Figure 10:
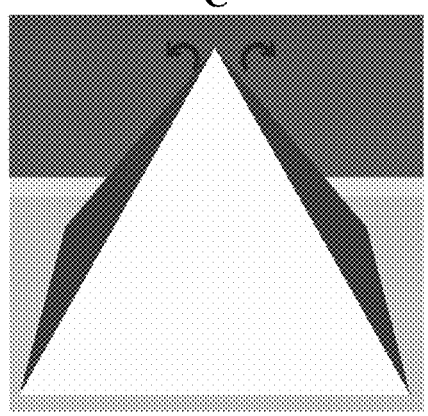

Union—This tool is used to define a region boundary based on the addition of two object volumes (FIG. 9).

Object Map—Defined boundaries may be tracked and defined objects may be presented to the user in a color coded object map. This allows the user to easily visualize the individual components of their 3-D model.

Annotation—A text annotation tool may be added to the application. The text annotation tool permits a user to add text notes to a selected edge or filled region. An option exists added for leader lines to point out the area of interest for a note that is added.

Measurement—This tool allows users to draw point to point measurement lines on both a 2-D image slice and within a 3-D model. This may be useful, for example, when the user is dimensioning the 3-D model for printing. In addition, a scale bar and a reference object (such as a coffee cup) may be supplied in the 3-D modeling environment.

Advanced User 2-D Image Editor User Interface—This interface presents data to a user as a sequence of grayscale two-dimensional slices, with intensity determined by the density of the tissue. Structures are identified and isolated using the varying intensity as a guide. Isolation of a structure is accomplished by creating free-form bounded regions on each slice, which are then connected together between the slices to calculate an isolated volume.

TSIM also provides different tools for controlling image properties, such as brightness and contrast, and for image editing (e.g., annotations and object definitions). A loaded image set will be displayed below the image workspace using scrollable image previews. Within the image workspace, a 3-D rendering of the image set will be displayed with three image views that can be collapsed. Exemplary views include axial, sagittal and coronal views which, for example, may be located in the upper left corner, bottom left corner, and bottom middle of the screen when restored.

Exemplary Image Property Control Tools:

Brightness, for increasing or decreasing the tonal values of the image

Contrast, for expanding or shrinking the overall range of tonal values in the image.

Window Midpoint which may be represented as a dial that can be used to adjust the midpoint of the density mapping into grayscale for the image being viewed.

Window Range for expanding or shrinking the visible density range of the image being viewed.

Filters numerous filter presets may be available for the user to apply to the image set.

2D Rectangle Inclusion Tool permits the user to define a rectangular region of interest within a 2D image. After the region has been defined by the user, the 3D model will then update and exclude all data that was not included in the region of interest.

Image Reset Tool reverts the image processing to the original 2D image levels.

2D Boundary Definition Tools

Point Spline—This tool is used to define a region boundary from a closed spline created from a series of control points. Each input within the image area will add a new control point. If desired, TSIM will automatically adjust control points to better fit the boundary to nearby detected edges. After the boundary has been completed, the user may directly adjust the position and parameters of any control point, as well as add or remove control points. Once the user is satisfied, they can confirm the boundary and a region object will be created. The Point Spline Tool acts as an editor if the user would like to make changes to these region objects in the future.

Free Form—This tool allows the user to create a spline from a free-form sketch. After creating a sketch, the software fits a spline to the sketch. The user may draw over this spline to refine the shape. Once the user is satisfied, they can confirm the boundary and a region object will be created. The Point Spline Tool acts as an editor if the user would like to make changes to these region objects in the future.

Duplicate—This tool copies bounded regions from one image slice to another. This tool may be used to avoid the effort of creating regions when the differences between image slices are minimal. After duplicating regions, the user may use the Point Spline Tool to make any necessary corrections.

The TSIM User Interface (UI)

The TSIM UI displays the planned print path of the 3-D model and the current print head location along the path in real time. In addition, the printer's current state regarding the parameters of active nozzle, pressure, and speed is displayed along with an active print duration. A chart showing the amount of material used by the printer may be displayed on the right-hand side of the UI. Below the print path, a scrollable timeline may be generated that allows the user to track the progression of the printed material throughout the print cycle. Dialog boxes may pop up if an error is encountered in the printing process. For example, if the printer runs out of material in a cartridge, a dialog box will pop up on screen that says, "Fill Reservoir 2 with Gel 2."

A TSIM object modeling screen provides a 3-D environment for designing/creating models, or for importing existing models for the purpose of printing/fabricating via the robotic workstation. Complex models may be created using a basic set of geometric shapes. An illustrative provided set of geometric objects comprises box, cylinder, sphere and pyramid shapes. Manipulation tools include, but are not limited to providing functionality of combining, aligning, sketching, volume-rendering, surface-rendering, and the like. Models may be opened for solid modeling in a variety of standard imaging formats, including for example STL, DICOM and NIfTI formats. An Exemplary TSIM operations panel is depicted in Figure X.

Each object added to the object modeling environment is associated with an object property list such that the object property list is displayed upon adding a selected object to the modeling environment, and a composite object property list is displayed comprising an objected property list for each object added to the modeling environment. Figure X depicts an exemplary modeling environment including four selected objects and a corresponding composite object property list. The objects are selected from cube, cylinder, sphere and pyramid. Selected or created objects may be given unique identifiers by the user.

Key Frame Automatic Bounding Support.

TSIM includes a Key Frame Automatic Bounding Protocol in which intermediate region boundaries will be extrapolated between two non-adjacent image slices. Typically, these two images will provide the clearest views of objects within the images that the user wants to define. The user will select two non-adjacent image slices as key frames and execute the Extrapolate command. This command tells the program to extrapolate those defined features through the images in between the defined key frames using the edge detection algorithm.

Extrusion Material Assignment Tool.

This tool allows the user to specify a set extrusion material for defined objects in the 3-D model or to define regions of the 3-D model as consisting of a certain material. For the first case, the user selects the tool, the extrusion material, and then the desired object(s). For the second case, the user may define areas using existing splines or by drawing a spline and then selecting the tool. The user may then either specify the program to define a material region from a spline using a specified thickness or by extending the region to another spline.

Printing Support.

Assembly Monitoring—This functionality allows the user to monitor the assembly of tissue constructs using a mounted camera located within the printer. Once this option is enabled, a video feed appears in TSIM that streams until the printing process is finished.

Digital Prototyping—Simulation Tools—A suite of simulation tools are available within the Simulation module of TSIM. There is a tool for estimated print time (Print Time tool), required volume for extrusion (Volume tool), and structural analysis of the 3-D model (Structural Analysis tool).

Print Time Tool—This tool estimates and displays the time (in minutes) that it will take to print the created 3-D model.

Volume Tool—This tool estimates and displays the volume of extrusion material that is required to print the user's 3D model.

Structural Analysis Tool—This tool allows the user to perform a structural analysis assessment on the 3-D model to estimate its stability once printed. This tool is based on the principles of smooth particle hydrodynamics.

Material Database

A materials database is available and defines what extrusion materials are available to the user when modeling tissue constructs. Users are able to find their desired materials by searching all of the available materials, browsing all of the available materials, or searching available materials by application. This materials database permits users to add or edit entries, with delete functionality reserved to the Local Database of the user. In addition to pictures of the materials, information stored for the materials will include parameters such as material type, viscosity, weight percent (in solution), Young's modulus, stress, and strain.

Local Database. A local database comprises a basic materials database including pre-set materials. The user may then expand upon this database and save new entries on a local machine.

A specific fabrication material may be assigned to each object, and each material is associated with a dispensing needle type (length, diameter) and operational parameters including pressure, speed, acceleration, on/off delay and cure methods. Once assigned, a material selection and material details may be edited in accordance with test print feedback and/or specific application needs. In the alternative, a user may create a custom materials menu adapted to specific application needs.

Once added to the modeling screen, an object may be transformed. In specific embodiments, a transform function selection panel is provided. In very specific embodiments the object may be transformed by moving the object and/or modifying the center coordinates of the object. Other examples of transforming functionality include rotating an object about its center coordinates, for example by dragging individual roll, pitch or yaw sliders or by dragging an individual block in a desired direction, and scaling an object, for example by scaling via a uniform xyz scale factor or by scaling along an individual axis. In very specific embodiments transforming functionalities are reversible.

Once designed, models to be printed/fabricated are sent to the RBW using the TSIM software. The RBW comprises a tabletop workstation including a multi-axis robot that facilitates 3-D tissue printing of composite volumetric shapes and assembly of biological constructs. The robot comprises at least six axes of fabrication orientation making it particularly suitable for the level of precision required to assemble functional tissue structures. According to one embodiment, the RBW comprises a multi-axis robot, a robotic controller (in preferred embodiments the controller is located outside the RBW housing or is separately contained within the RBW housing), a frame defining a housing, a print stage, at least one robot end effector, at least one material storage unit, and a unit interface (in preferred embodiments the RBW-UI is located outside the RBW housing). In specific embodiments the robot comprises an arm having at least a six-axis range of motion. In very specific embodiments the robot is selected from an EPSON C3 series compact 6-axis robot compatible with a PC based controller and or the EPSON RC180 and RC620+PC based controllers. A frame may comprise one or more of the following features: a Bosch aluminum T-slot, doors, floor, ceiling, roof, paneling, and lighting. A print stage may be constructed of any suitable material and in specific embodiments comprises a leveling mechanism. In preferred embodiments, the robot is situated over and above the print stage. A Robot end effector comprises one or more of a pneumatic gripper, syringe barrel holder, camera, laser displacement sensor, auto-leveling chuck, and cable management. In specific embodiments a material storage unit comprises a syringe holder, displacement sensors and a station mount. The electrical design includes a pneumatic feed line and an electrical power cable. The workstation may be provided in mobile form, for example on a cart.

The RBW User Interface (UI) comprises a status screen which provides the user with information relating to the current state of the workstation. From the status screen a user may, for example, monitor the proper functioning of the RBW's components, such as the controller, dispenser and microcontroller, view a streaming video feed of print jobs, and follow-up on any alarms indicating attention required before proceeding.

The RBW-UI further permits a user to make offsets, which is a minor modification made in real-time based on empirical observation. Offsets may be made for pressure, vacuum, speed and Z-height and acceleration values, for example.

Figure 1:
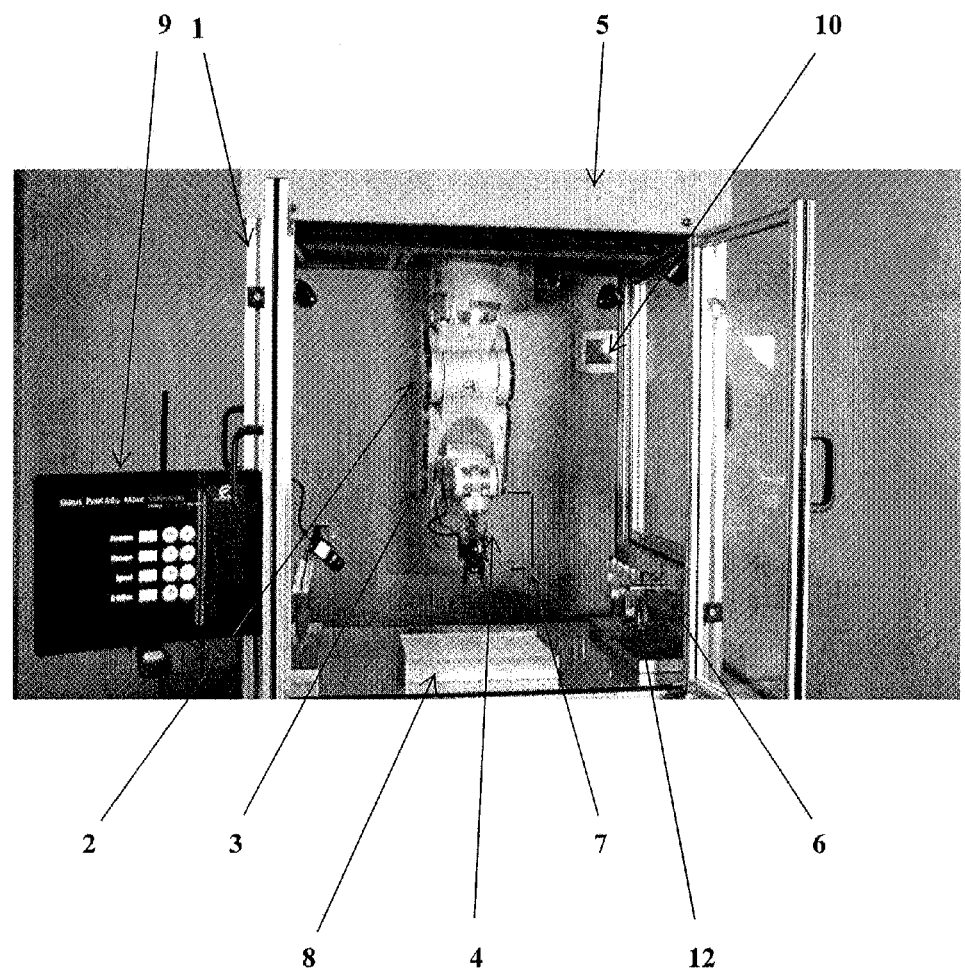
FIG. 1. Depicts an illustrative robotic bioassembly workstation (RBW).
Figure 2:
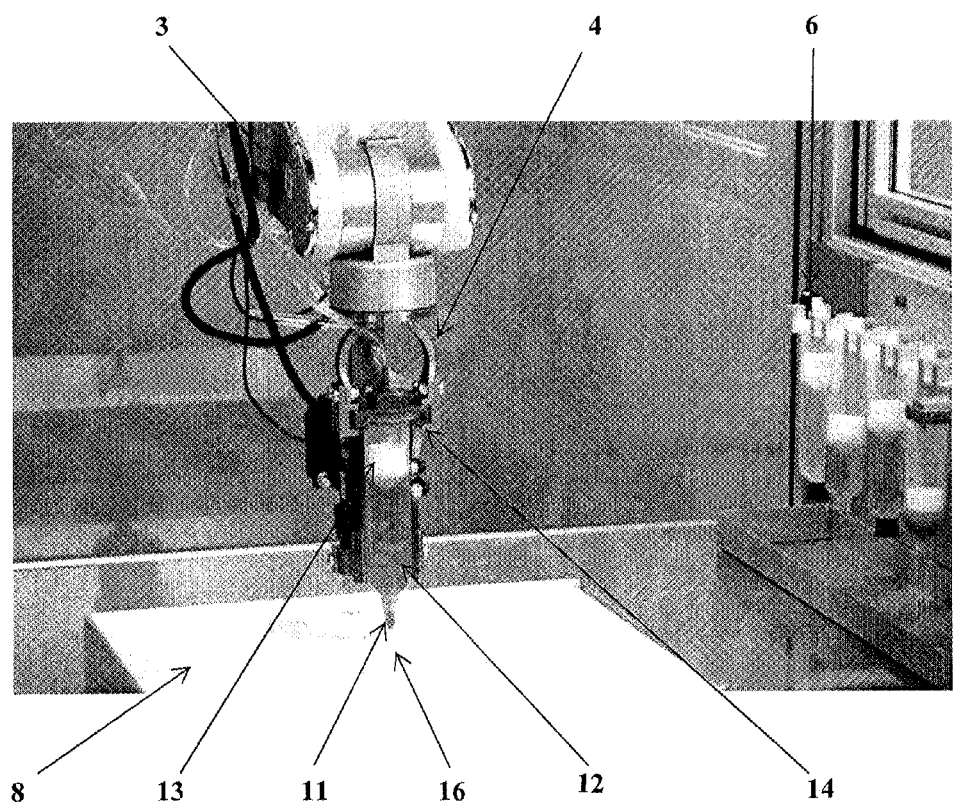
FIG. 2. Depicts an illustrative RBW robotic arm effector gripping a syringe barrel loaded with biomaterial and positioning the syringe for printing over printing stage.
Figure 3:
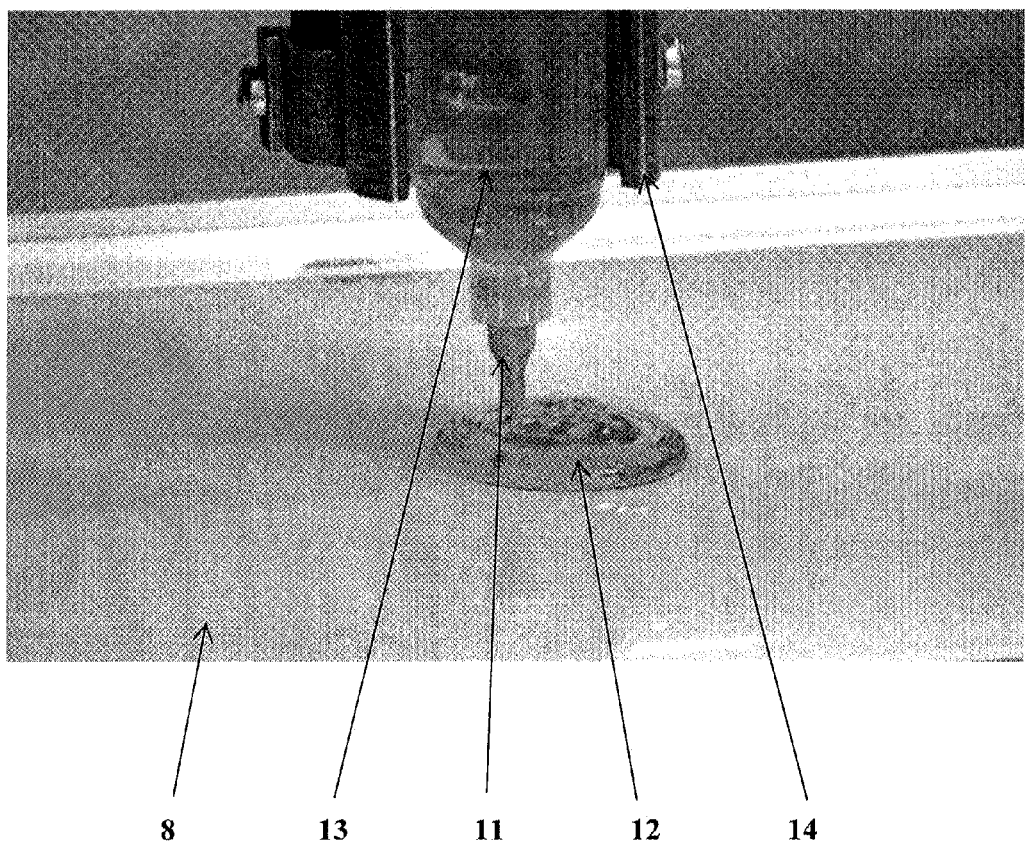
FIG. 3. Depicts exemplary printing of biomaterial via direct-write dispensing from a biomaterial-loaded syringe.

Features of the robotic bioassembly workstation are described now with reference to specific embodiments depicted in FIGS. 1, 2 and 3. It should be noted that this discussion is for illustrative purposes, and a person of ordinary skill in the art will appreciate that various configurations are possible without departing from the scope of the invention as defined by the claims. As depicted in FIG. 1, an RBW comprises a framed housing 1 comprising a multi-axis robot 2 comprising a robotic arm 3 having a robotic arm effector component 4, a robotic controller 5, a material storage unit 6, a material dispensing system 7, an adjustable print stage 8, and a user interface 9. In preferred embodiments the framed housing is operationally accessible to a user from multiple angles and provides at least one real-time observation access. The RBW may also be fitted with a camera 10 as part of an intelligent visual feedback system to supplement empirical observation and/or to provide remote viewing options, as well as the ability to stop a print/assembly process and make adjustments.

The bioassembly system comprises a multi-axis robot 2 and in preferred embodiments is a six-axis robot. In specific embodiments the material dispensing system 7 comprises extrusion syringe dispensers 11 adapted for direct-writing a biomaterial 12 onto a substrate. Due to the increased degree of freedom of the six-axis system, dispensing of biomaterial may be effectuated at an angle oblique to a plane of a surface of a printing substrate.

In specific embodiments, the robotic arm effector component 4 comprises one or more effectors selected from printing tools, staging and assembling tools, and sensors, and the system further comprises automatic tool exchange functionality for effectuating automated exchange of tools at the effector component as dictated by the print and/or assembly command. According to specific embodiments, printing tools are selected from a gripper, a syringe barrel 13 adapting holder 14 and a dispenser 11. Staging and assembling tools are selected from picking, placing, and positioning tools, and sensors are selected from a laser displacement sensor and a photoelectric sensor. In certain embodiments the RBW comprises a print stage 8 leveling mechanism. In specific embodiments, a laser displacement sensor is located on the robotic arm effector 4. The laser displacement sensor enhances a manual leveling protocol.

Staging in accordance with certain embodiments may include picking and placing a print substrate onto the print stage. Printing is then effectuated on the substrate, which in very specific embodiments may include variable surface topographies designed according to needs of specialized constructs. Assembling an ultimate bioconstruct may be effectuated by, for example, picking and positioning a first printed construct relative to a second construct, the second construct selected from a second printed construct and a provided construct. The print stage 8 may be partitioned into areas, for example a print area and an assembly area, and non biological constructs may be included for assembly with biological constructs. Medical devices and jigs may be comprised entirely of non-biological materials; however fabrication may proceed similarly and advantages conferred by the bioassembly system for the fabrication of biological constructs also generally apply to non-biological constructs.

Generally, the material dispensing system 7 comprises multiple syringes 11, each syringe containing one material or bio-material 12, and dispensing from a syringe 11 comprises dispensing one material or biomaterial 12 at a time. The material storage unit 6 comprises at least one syringe barrel holder 14. Each syringe barrel holder 14 comprises multiple syringe barrels 13. The material storage unit 6 may also include at least one displacement sensor for ensuring correct seating of syringe barrels 13 in the holder 14; and at least one needle detection sensor for detecting needle 16 size and tip deflection.

One embodiment is directed to a robotic biomaterial dispensing apparatus comprising a robotic arm and a robotic arm end effector, the end effector configured to grip and secure a dispensing syringe, wherein the robotic arm provides movement of the syringe along at least six axes. The ability to move along six axes permits novel functionality, in particular with respect to printing on 3-D print substrates. Bio-constructs may be fabricated, for example, by dispensing biomaterial onto a print substrate without being restricted to sequential layering as with conventional bio-printer designs, which rely on fabricating complex constructs such as tissues and organs layer by layer. With six axes, biomaterials may be dispensed by non-sequential planar layering such that the robot effector may return to a prior layer and add more biomaterial after dispensing a subsequent layer. Further, the robotic effector is capable of aligning a dispenser/syringe tip at an angle normal to any point on a contoured surface. This provides a higher degree of 3-D printing versatility and permits a wider variety of surface contours to completed constructs, and with respect to objects derived from medical imaging, provides potential for construction from a radial geometry, utilization of polar or hybrid polar coordinate systems, and therefore greater 3-D precision. Specific embodiments are directed to methods of fabricating a 3-D biological construct comprising direct-write dispensing of one or more biomaterials onto a 3-D print substrate utilizing the robotic biomaterial apparatus according to claim 24, wherein the robotic arm end effector positions the dispensing syringe at an angle normal to all positions on a surface of the 3-D print substrate.

EXAMPLES

The Following Examples are set forth to illustrate certain aspects, features and advantages of embodiments of the instant invention and should not be construed as limiting the scope of the invention as defined by the appended claims.

Example 1

This Example illustrates creation of simple objects in the object modeling environment.

A. Create a box (FIG. 7)
1. Click on the Create a Box icon.
2. Click the location on the modeling environment to begin placing the Box.
3. The size of the Box's base can be adjusted by moving the mouse accordingly. To accept, click the left-mouse button to set the base.
4. Moving the mouse vertically sets the height of the Box. To accept, click to set the height. Further refinements to the dimensions of the Box can be made by manually editing the center's coordinates or changing the length/depth/height of the Box.

B. Create a Sphere in the modeling environment (FIG. 8).
1. Click on the Create a Sphere icon.
2. Click the location in the modeling environment on which to place the sphere.
3. The size of the sphere can be adjusted by moving the mouse. To set the size, click once more. The sphere may be further refined by manually entering the center's coordinates or changing the value of the radius.
4. To accept the final shape, click the Create Solid button on the Sphere menu.

C. Create a Cylinder in the modeling environment (FIG. 9)
1. Click on the Create a Cylinder icon.
2. Click the location in the modeling environment on which to place the cylinder.
3. The size of the cylinder's base can be adjusted by moving the mouse. To accept, click to set the base.
4. Next, adjust the height of the cylinder by moving the mouse and clicking once more to set it.
   Dimensions of the cylinder may be further refined by manually entering the center's coordinates or the value of the radius or the height.
5. To accept the final shape, click the Create Solid.

D. Create a Pyramid in the modeling environment (FIG. 10)
1. Click on the Pyramid Tool icon.
2. Click the location in the modeling environment on which to place the pyramid.
3. The size of the pyramid's base can be adjusted by moving the mouse. To accept, click to set the base.
4. Next, set the height of the pyramid by moving the mouse. To accept, click to set the model.
5. The dimensions of the pyramid can be further refined by manually entering the center coordinates or the value of the radius or height.
6. To accept the final shape, click the Create Solid.

Example 2

This Example illustrates manipulation of the objects in the object modeling environment. The objects added to the object modeling environment may be further manipulated, for example by combining, moving or aligning objects. In particular embodiments, objects may be combined to form unique/customized shapes. Operations for combining may include adding (union), subtracting (difference) and/or intersecting objects in the modeling environment.

Figure 11:
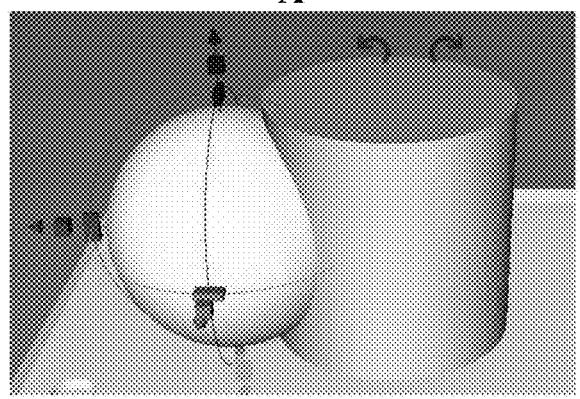
FIG. 11. Depicts specific modeling environment screens illustrating a simple addition operation; 11A select first object; 11B select second object; 11C click addition operation icon to form unified object.
Figure 11:
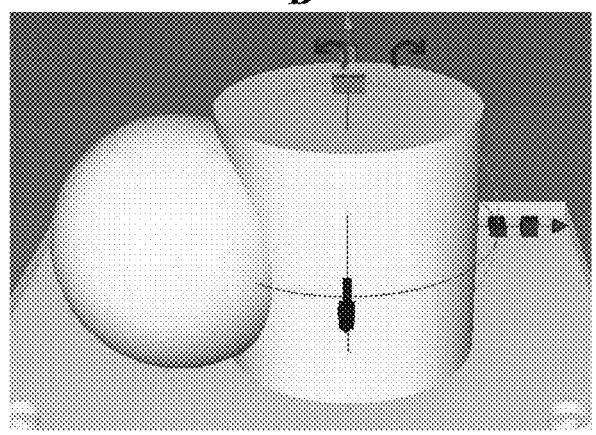
Figure 11:
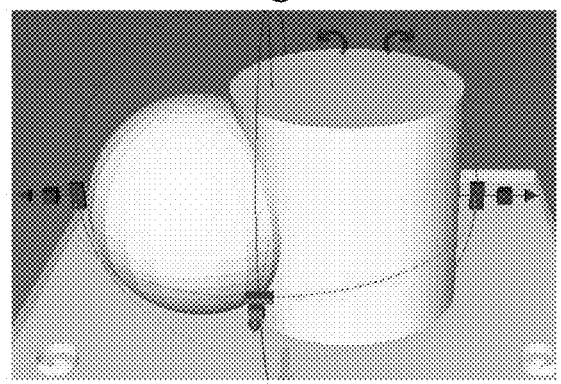

A Union/Combine operation comprises merging together two separate object volumes so that their boundaries will be defined as a single region. A union operation is illustrated in FIG. 11.

Figure 12:
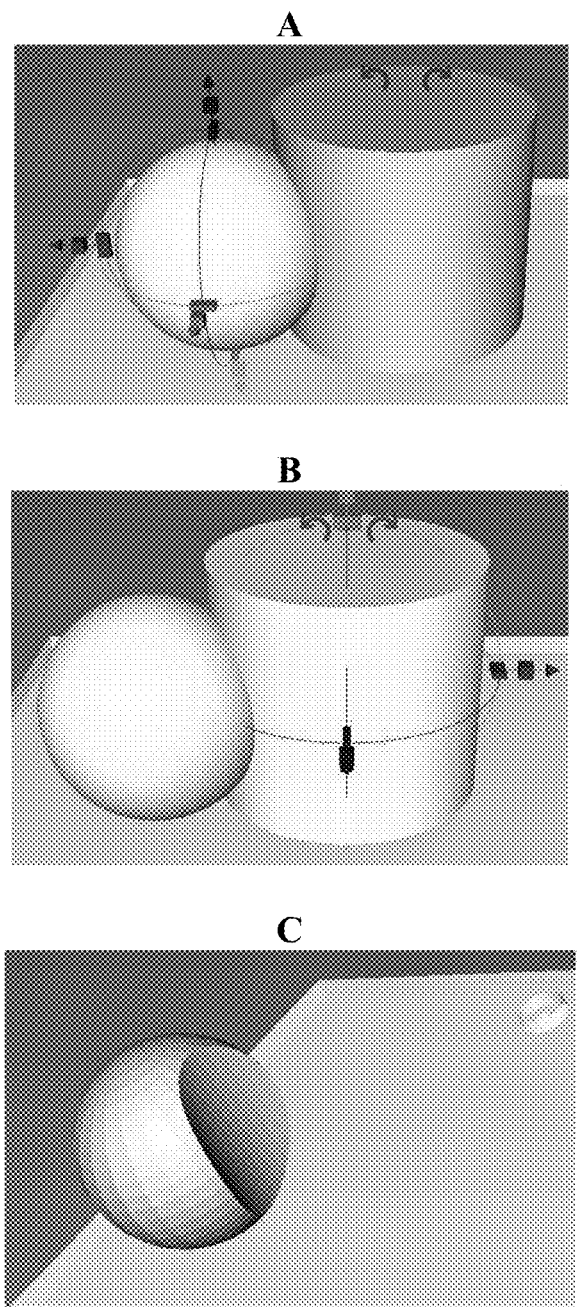
FIG. 12. Depicts specific modeling environment screens illustrating a simple difference operation; 12A select active object first; 12B select inactive object next; 12C click difference operation icon to leave portion of active object that does not intersect with inactive object.

A different operation is used to define a region boundary based on the subtraction of an actively selected object from an inactive object. A difference operation is illustrated in FIG. 12.

Figure 13:
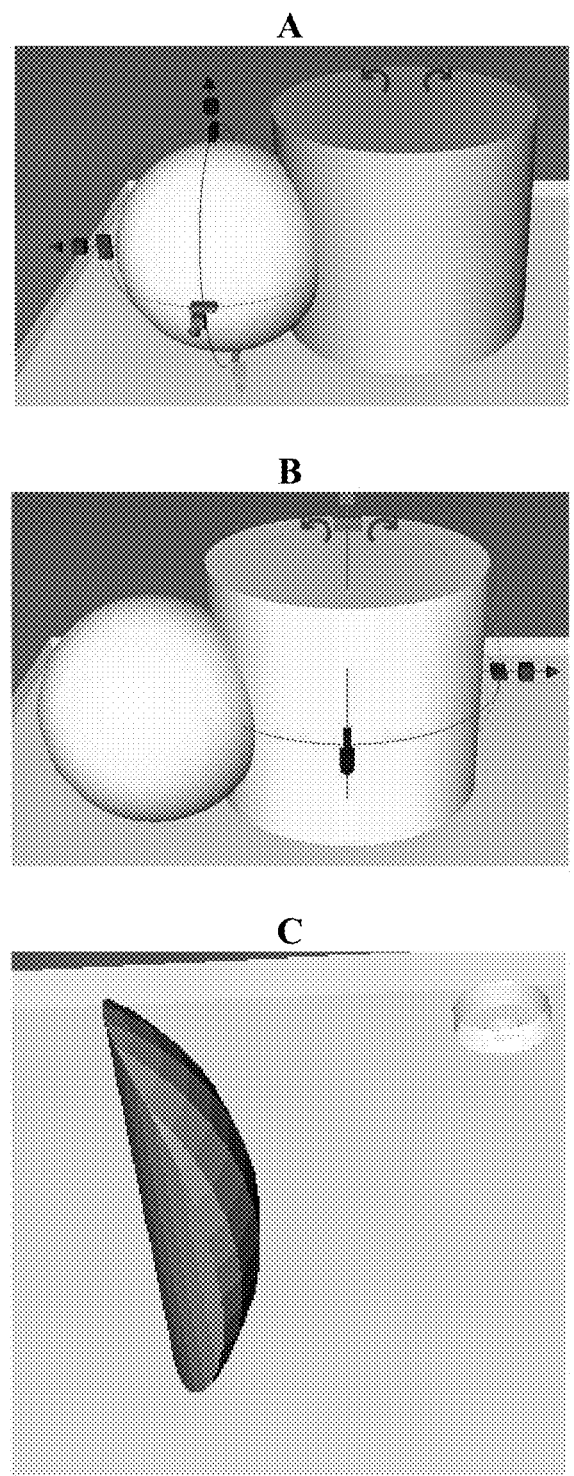
FIG. 13. Depicts specific modeling environment screens illustrating an intersection operation; 13A select active object as first object; 13B select second object; 13C click intersection operation icon to leave portion of active object that intersects with first and second objects.

An interesection operation is used to define a region boundary based on the intersection of two objects. An intersection operation is illustrated in FIG. 13.

Figure 14:
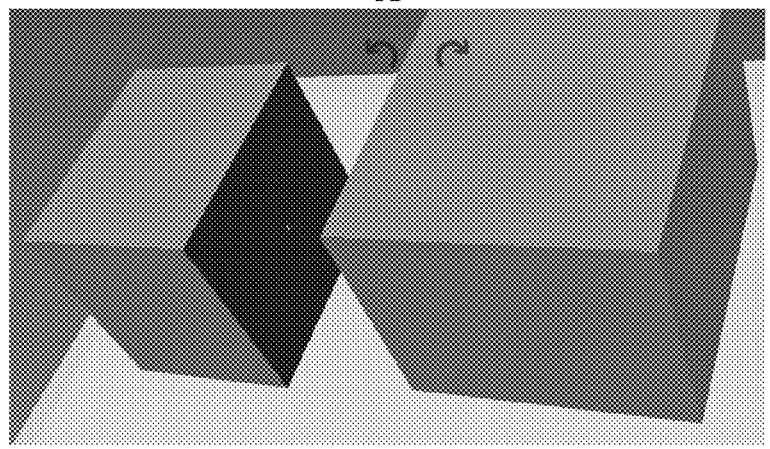
FIG. 14. Depicts specific modeling environment screens illustrating an alignment operation; 14A select a point on desired face of first object; 14B select point on desired face of second object; 14C click align operation icon and first object will move such that points on selected faces align.
Figure 14:
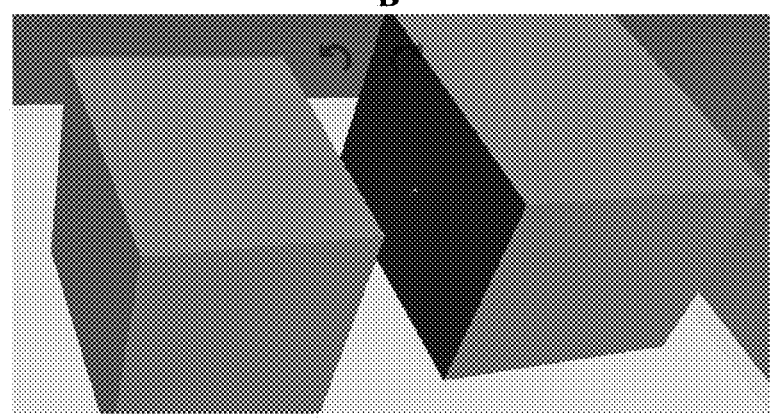
Figure 14:
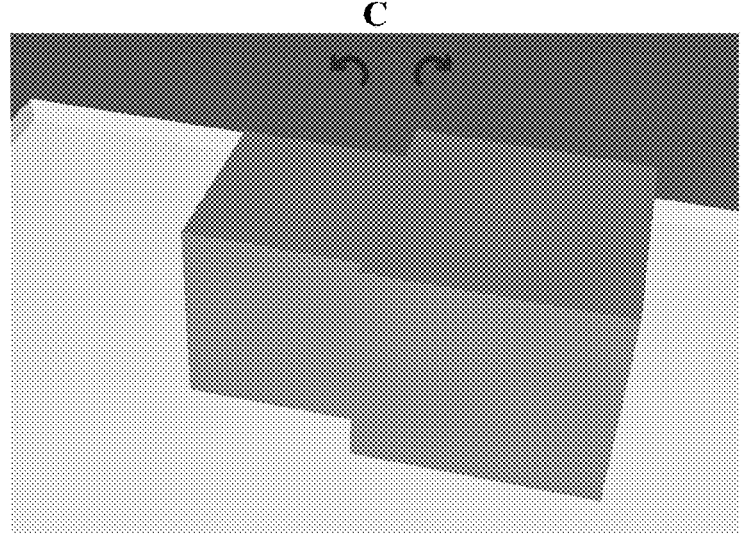

Functionality for aligning objects in the modeling environment is also provided. In specific embodiments, two faces on different objects may be aligned based on a point selected on each shape, as illustrated in FIG. 14.

In other specific embodiments, objects may be aligned along the y-axis, x-axis or z-axis based on center points of selected facades/sides. A move operation permits movement of objects into different positions without necessarily aligning (FIG. 15A).

Figure 15:
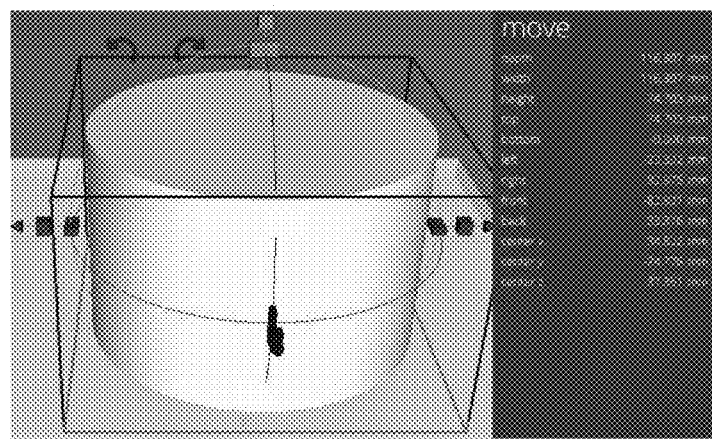
FIG. 15. Depicts specific modeling environment screens illustrating two more TSIM operations; 15A dragging; and 15B measuring.
Figure 15:
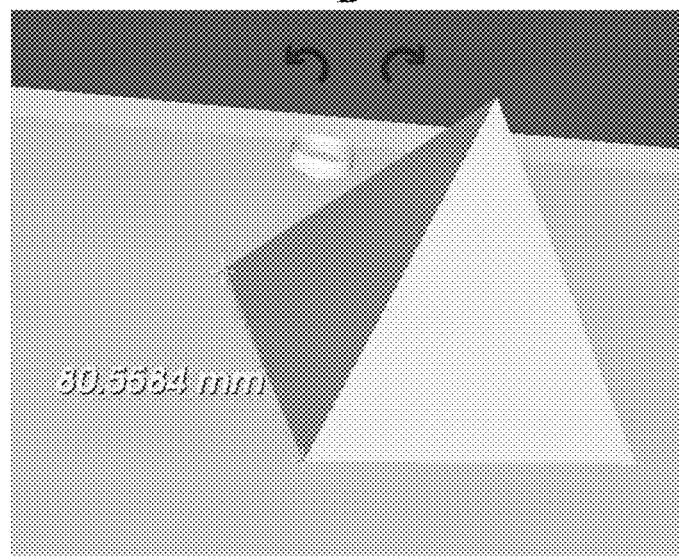

A dragging operation, as illustrated in FIG. 15B, permits moving a selected shape in different directions relative to the "ground", which is determined based on a camera angle. In one specific example, in a default view, dragging a model will move a shape in the xy-plane.

A measuring operation permitting point to point measurement lines on both the 2-D image slices and within a 3-D model is also provided and illustrated in FIG. 15B.

Example 3

This Example illustrates importing objects directly into the modeling environment from other programs. Users may open existing model files created in external programs. Exemplary importable file formats include STL, NIfTI and DICOM.

Importing an STL file.
1. Click on the Import STL icon in the Import section.
2. Navigate to the folder containing the STL files.
3. Highlight the desired file and click the 'Open' button to import the model.
4. The object will appear in the modeling environment. As in the case of shapes created in TSIM, modification of the imported object is via the Objects menu on the right-hand side.

B. Importing a NIfTI file.
1. Click on the Import NIfTI icon in the Import section.
2. Navigate to the folder containing the NIfTI files
3. Highlight the desired file and click the 'Open' button to import the model.
4. The object will appear in the modeling environment. As in the case of shapes created in TSIM, modification of the imported object is via the Objects menu on the right-hand side.

Figure 16:
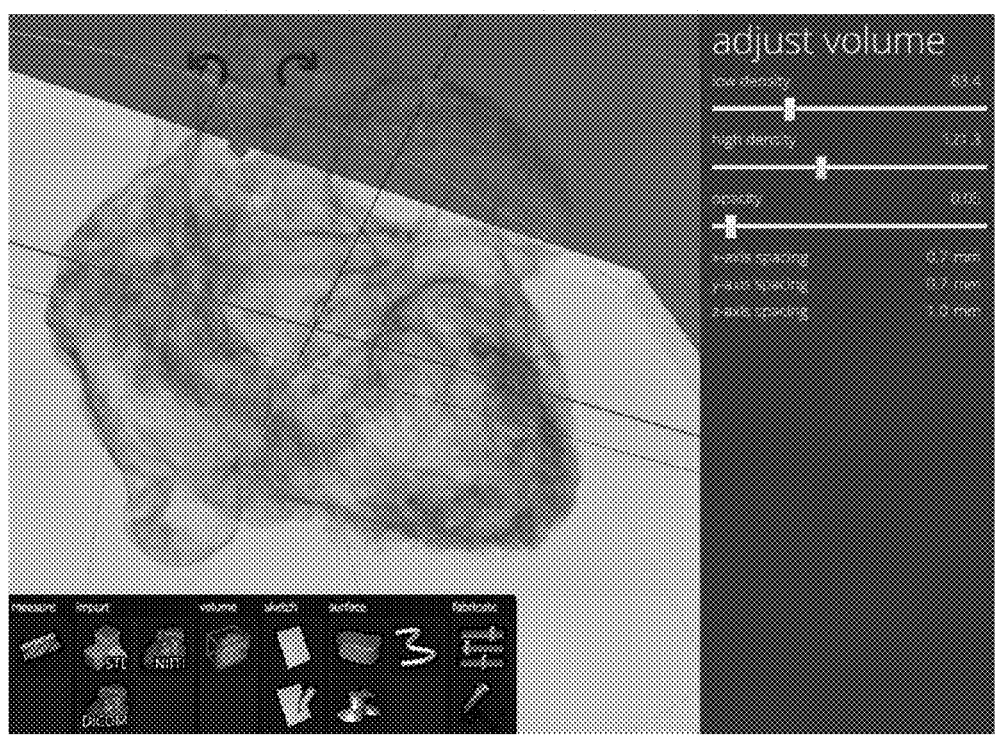
FIG. 16. Depicts a specific modeling environment screen illustrating adjusting the volume of a DICOM image imported into the object modeling environment.

C. Importing a DICOM file.
An example of an imported DICOM image is depicted in FIG. 16.
1. Click on the DICOM icon in the Import section.
2. Navigate to the folder containing the DICOM files.
3. Click 'Select Folder' to import the model.

Example 4

This Example, taken with FIG. 16, illustrates a volume operation, which permits further analysis of a volumetric model (e.g. NIfTI or DICOM) by adjusting density or opacity values. The spacing values for each axis may be modified as well.

Import the volumetric file

Click on the Volume icon

Click on the imported model to highlight it. The Adjust Volume menu will now be displayed on the right hand side. By adjusting the individual sliders, you can change the respective value, which in turn updates the model. The viewing angle may be changed while making adjustments to the volume.

Example 5

This Example illustrates a sketch operation according to specific embodiments.
1. Click on the Create a sketch icon
2. The three individual planes will appear in yellow. To choose the plane onto which a sketch will be drawn, click on a desired plane.
3. The chosen plane will now appear highlighted in blue together with the interaction widgets. The plane may be moved or rotated.
4. Click on the Create button to begin working on a sketch.
5. If selection of a different plane is desired, choose the Select a New Plane button to return to Step 2.
6. The selected plane will now be displayed as a grid and the Sketch menu will appear. Custom shapes may be drawn by using curves, circles, points, rectangles, etc.
7. Once a shape drawing is completed, right-click to stop drawing and click on the Select tool to return back to the Solid Modeling screen.

Sketches may also be modified and managed.

More complicated shapes may comprise a collection of sketches made on different planes. Managing operations permit users to modify, move, delete or hide individual sketches in a collection. Sketches may be interacted with individually via the sketches menu.

Example 6

This Example illustrates extrusion of a sketch into a 3-D model (FIG. 17).
1. Begin with an overhead view of the sketch.
2. Next, hold the CTRL key and click on each of the individual sides of the sketch. Selected sides will be highlighted in blue.
3. A wire frame of the shape is displayed when all sides are connected. The Extrude menu on the right side will now be active and allows adjustment of both the length and resolution of the extrusion.
4. Click on the Extrude button to create the final shape.

Example 7

Figure 18:
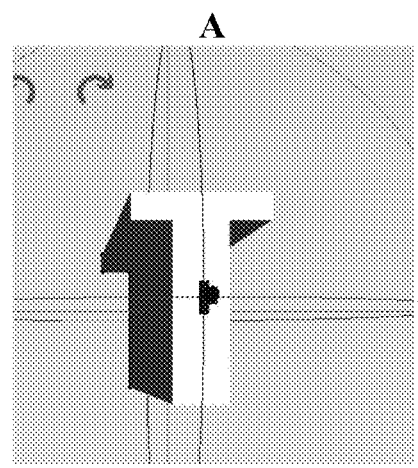
FIG. 18. Depicts specific modeling environment screens illustrating creation of new volumetric objects by lofting contours; 18A lofting contours of a solid T-form; 18B sketches setting base and top surfaces to create a volumetric object; and 18C lofting contours of the volumetric object to create a new object.
Figure 18:
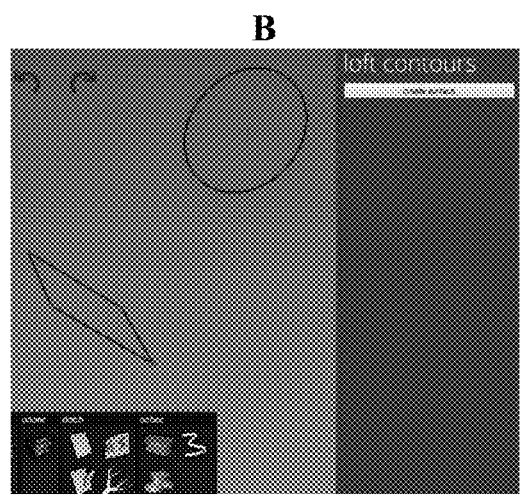
Figure 18:
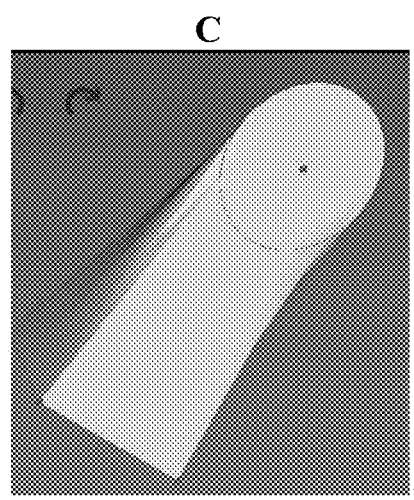

As shown in FIG. 18, new shapes may be created by connecting boundaries of sketches rendered on different planes, with further modification possible by lofting contours.

Example 8

This Example illustrates utilization of the TSIM functionality to model a vascular tree (FIG. 20), which may then be fabricated via the RBW.

According to one specific embodiment, the method comprises entering in a set of input parameters such as those set forth in Table 1.

TABLE 1

| | |
|---|---|
| Starting diameter (μm) | Diameter of the largest vessel at the initiation end. |
| Order length (μm) | length of an order. |
| Ratio | Determines the decrease in size by ratio of diameter from one order to the next. |
| Number of orders | The number of steps down in the branching pattern |
| Ending diameter (μm) | Diameter of the largest vessel at the terminal end. |

Once a model is generated, specific materials may be assigned to each order of the vascular tree. In specific embodiments, the RBW stages the print stage with a mold or other substrate having a variable surface topography on which to print a vascular tree. Printing of other complex tissue constructs may also require staging by picking and positioning substrates as printing surfaces into the print stage. In some specific embodiments, a print stage may be divided into a print area and an assembly area so that a bio-construct may be assembled as it is printed on a component by component basis.

Example 9

This Example illustrates modeling of a 3-D tube from a sketched curve, further as depicted in FIG. 19. Radius and resolution of a generated tube may be directed and modified.

Example 10

Figure 21:
FIG. 21. Depicts a very specific exemplary print screen at the TSIM-UI.

This Example, taken with FIG. 21, illustrates initiation of printing by the robotic bioassembly workstation.

Print job is chosen from the list. A preview is available under the Project Preview, Press Start After a successful password prompt, a material loading process can begin.

In very specific embodiments, once a print job has been chosen and started, the UI will prompt the user to physically load the individual barrels into specific slots on the material storage unit. Once loaded, the user confirms before moving on to the next material. Visual indicators may be present to provide a status update of each of the material holder bays. Table 2 is illustrative of this concept.

TABLE 2

| Color | Meaning |
|---|---|
| Grey | The specific bay is occupied with a barrel. |
| Green | Load the material in this bay |
| Red | Incorrect material placed in the bay. |

A "Move" operation permits manual adjustment of positioning of the robot to place it into a desired position via the RBW-UI screen. The robot may be adjusted along any axis and the robot may be restored to a "home" position. Other control operations may include resetting power to a controller, adjusting and turning on the pressure (psi), turning off individual joint brakes (J1 through J6, one J for each movement axis). A calibration menu ensures that the workstation is setup accordingly ahead of any prints made.

Example 11

This Example illustrates an embodiment of a materials testing protocol prior to printing/fabrication. When utilizing a material for the first time or under unique condition parameters, it is important to test printing quality at various needle diameters, speeds, pressure, etc.

Exemplary steps to conducting a material test include:
1) Manually attach a syringe with a new material to the robot's end effector.
2) On the RBW-UI, press the Material Test option under Calibration.
3) A grid of the printing platform will be displayed. To begin, press one of the cells in the grid to select it.
4) Increment or decrement the desired parameter value for that cell by pressing the respective plus or minus sign. Alternatively, click in the value box for a parameter and use the on-screen keyboard to enter desired values.
5) Press Save to set the values for the selected cell.
6) If desired, choose another cell and repeat steps 4-5.
7) When ready to print, press Start. Please note, the Start command does not appear until values for at least one cell are saved.

A completed print will be lines printed with the material and it can be determined which group of settings best meets specific application needs.

Example 12

This Example illustrates print stage/platform leveling functionality.

A level print stage is intrinsic to producing quality prints. In specific embodiments, the RBW-UI provides feedback relating to the degree to which the stage is level and what modifications may need to be made to perfect leveling.

To begin leveling:
1) Press the Leveling option located under Calibration.
2) Press Start to begin the leveling test.
3) As the robot moves to a position near each stage bolt, the height of the print platform is determined. At the conclusion of the test, a user is prompted with the exact adjustment to raise or lower the individual corners.

The distance from the top of the robotic arm to the center of the stage must also be calibrated. A tip sensor is detected and position is determined. An offset of barrel to sensor is determined and a pressure displacement curve is calculated.

Example 13

This Example illustrates exemplary components and component-associated functionality of a very specific embodiment of the RBW according to the disclosure. Reference is to elements designated in FIGS. 1, 2 and 3.

Housing

Frame: According to one non-limiting exemplary embodiment the frame is an aluminum T-slot Frame. For example, the RBW physical frame may be constructed using a combination of Bosch T-Slot Profiles, Doors: The doors of the RBW are constructed using Bosch T-Slot Profiles with clear, scratch-resistant polycarbonate inserts to provide users with visibility of the inside of the station.

Floor: The RBW floor may be a solid ⅛" thick aluminum sheet with three holes for mounting and adjusting the print stage.

Ceiling: The RBW ceiling may be a solid ¼" thick aluminum sheet.

Roof: The RBW roof may be a solid ¼" thick dove-grey acrylic sheet.

Fascia Paneling: The fascia paneling of the RBW can be constructed using ¼" thick dove-grey acrylic sheets. In preferred embodiments, panels utilize M5 black knurled head thumb screws to fasten to the frame. Panels are removable to allow users access to the station control panel.

Lighting: The RBW may have four white LED lights (IP68 rated) mounted in the four corners of the station to enable a camera on the robot end effector to achieve a desired resolution.

2. Print Stage

Material of construction: The RBW print stage may be comprised of a solid sheet of acrylic. It may comprise three counterbore holes for recessing the bolt heads of the stage leveling bolts. In very specific embodiments, a leveling the bolts may be effectuated manually with a ratchet wrench.

Leveling mechanism: According to specific embodiments, the RBW print stage comprises three leveling bolts that insert into the through-holes of the three counterbore holes of the stage and extend down into three tapped mounting holes located in the channels of the support profiles below the floor of the station. A spring is wrapped around each bolt in-between the print stage and station floor. The diameter of the counterbore hole is such that a tool can be inserted to tighten or loosen the stage bolts.

Robot End Effector:

The robot end of arm tooling, herein designated as an "end effector," comprises components that attach to J5 and J6 (of the 6-axis robot) and includes print tools, assembly tools and sensors. Print tools include, e.g. a syringe barrel adapter holder and gripper.

Pneumatic gripper: According to specific embodiments, the robotic end effector comprises a pneumatic gripper mounted on its end, with gripping fingers oriented perpendicular to the centerline of the robot's J6 axis of rotation. The air feed to the gripper may be controlled by a solenoid valve that is turned on and off by the RBW control software. The gripper is used to grip one material syringe barrel at a time for the purpose of loading and unloading the barrels from the materials storing unit.

Syringe barrel holder: In very specific embodiments, a second piece of the RBW end effector connects a dispenser to syringe barrels, for example a Norson EFD Ultimus V dispenser to Nordson EFD 30 syringe barrels using an adapter assembly from Nordson EFD. This piece houses the adapter assembly from Nordson EFD on the end of axis J6 of the robot, allowing syringe barrels to be screwed into the assembly and extrusion to be controlled using Ultimus V dispensers.

Automatic tool change: According to particular embodiments, the RBW is capable of auto-changing from print/dispensing tools to specifically designed end-effector tools for pick and place of receptacles such as molds or containers to facilitate specific print applications. The auto tool change capability also enables the selection of tooling from the tool holder and used for assembling individual printed structures into more complex structures.

Camera: This element allows the user to monitor the printing of tissue constructs using a mounted camera located within the housing. Once this option is enabled, a video feed appears in TSIM and at the RBW user interface (RBW-UI) that streams until the printing process is finished.

Laser displacement sensor: In some embodiments, a laser displacement sensor is mounted on the end effector in parallel with the pneumatic gripper and syringe barrel adapter holder. This laser sensor is used to measure the distance between the print stage and end effector during the stage leveling process.

Photoelectric Sensor: A photoelectric sensor may be mounted on the end effector which allows the robot to detect placement of barrel holders when it is near. In addition, the sensor detects that the barrels are correctly picked up from the respective holder.

Material Storage Unit

Syringe holder: According to a specific illustrative embodiment, RBW houses four syringe holders and each holder contains three material cartridges for a total of 12 syringes.

Displacement sensors: The through beam sensor runs along the top of the material storage unit and checks to ensure the correct seating of the syringe barrels. In this exemplary embodiment there are eight through beam sensors located on the front and back side of each of the barrel holders. A stand-alone sensor (needle detection sensor), located at the bottom of the material storage unit, is used to detect the size of the needles and needle tip deflection for each of the syringe barrels.

Computer/Touchscreen (RBW-UI)

Location: In certain embodiments, the RBW-UI is comprised of a touchscreen computer mounted on a swivel arm located on an exterior part of the physical frame of the workstation.

Interface: The RBW-UI provides information about the printer's current state regarding the parameters of pressure and speed. A chart showing the amount of material used by the printer is displayed on the UI. The user is notified upon completion of print job. Dialog boxes pop up if an error is encountered in the assembly/bioassembly process. For example, if the RBW runs out of material in a cartridge, a dialog box will pop up on screen that says, "Fill Reservoir 2 with Gel 2."

The interface's Status option allows the user to check the status of the RBW by viewing the existing print jobs, a history, and a video feed of the assembly/bioassembly stage. The interface's Direct Control option provides the ability to job the robot to a desired location via the touchscreen.

In exemplary embodiments, the Leveling option may have the robot check one position near each stage leveling bolt and determines how level the print stage is using values obtained from the laser displacement sensor at each position. The Offsets option allows the user to manually set offsets. The Materials Testing option allows for the testing of materials with different parameters.

Controls Designs

Safety: Safety features comprise an emergency stop to shut down the robot entirely. Additionally, door locks may be included an added safety mechanism. Door locks halt operation in the event the door is opened during fabrication. Safety information for the EPSON C3 robot series can be found at http://robots.epson.com/product-detail/10.

Controls container: The controls container is securely mounted onto the RBW in the overhead controls area and serves as housing for the microcontroller.

Layout of overhead controls area: The overhead controls area consists of the controller, for example an RC180 controller, the controls container, the Nordson EFT Ultimus V dispenser, a 220 v step up transformer and associated components.

Microcontroller: Together with the printed circuit board (PCB) daughter board, the microcontroller interfaces between the HMI and the IO monitoring.

Printed Circuit Board (PCB)

7. Electrical Design

Pneumatic feed line: According to very specific embodiments, a single pneumatic quick connect receptacle is located on the right side of the RBW. Users connect input air line here. This line runs internally through the RBW to a regulator that then splits and feeds the line to the dispenser and solenoid valve.

In an illustrative embodiment, three pneumatic feed lines may then be routed to the robot. Two lines are used by the gripper. The remaining feed line is used to depress the barrel piston for dispensing.

Electrical Power Cable

8. Accessories

Mobile cart: In some embodiments, the RBW is housed on a mobile instrument cart. In very specific exemplary embodiment, the dimensions of the cart include two steel shelves 30"×40" with 1½" retaining lips, the overall cart height is 29" with a 27½" top shelf surface height and there are two swivel and two rigid 8"×2" phenolic wheels with wheel lock brakes on the swivel casters.

What is claimed:

1. A bioassembly system comprising a tissue modeling component and a robotic bioassembly workstation component, a hardware processor coupled to a memory, the tissue modeling component comprising a user interface, at least one suite of tools for performing an object operation selected from creating, editing, modeling, transforming, image property modulating, sketching, print supporting, simulating, material testing and combinations thereof, a material database, and software executable by a machine to facilitate a method for designing a volumetric model of a biological construct at the user interface, the tissue modeling component being operationally linked to the robotic bioassembly workstation component, the method comprising:

adding at least one object to an object modeling environment at the user interface, wherein adding comprises selecting, creating, importing, or a combination thereof, wherein adding an object to the object modeling environment comprises at least one of:

sketching a 2-dimensional bounded construct and extruding a boundary to form a model volumetric object;

sketching a 2-dimensional bounded construct on at least two different planes, connecting the boundaries of the constructs by straight or lofted contours to form a model volumetric object;

sketching an unbounded curve and selecting a diameter to form a model tube object; and selecting input parameters comprising starting diameter, order length, ratio, number of orders, and ending diameter to form a model vascular tree, and further wherein each added object is associated with an object list comprising material parameters;

performing one or more operations on the one or more objects in the modeling environment to render a desired volumetric model;

transmitting the rendered volumetric model to the robotic bioassembly workstation with a print and/or assembly command; and printing and/or assembling a bioconstruct in accordance with the rendered volumetric model.

2. The bioassembly system according to claim 1, wherein adding an object to the object modeling environment comprises selecting at least one object from a panel of stored objects.

3. The bioassembly system according to claim 2, wherein the panel of stored objects comprises one or more of a cube, a cylinder, a sphere and a pyramid.

4. The bioassembly system according to claim 1, wherein adding an object to the object modeling environment comprises importing an object by importing model files created in external programs, wherein the imported model files define medical images generated from a medical imaging technology.

5. The bioassembly system according to claim 4, wherein the medical imaging technology is selected from magnetic resonance imaging, computerized tomography, X-ray radiography, medical ultrasound, endoscopy, elastography, tactile imaging, thermography, medical photography and positron emission tomography.

6. The bioassembly system according to claim 4, wherein the medical images are specific to a patient and the rendered object model is personalized to specific needs of the patient.

7. The bioassembly system according to claim 1, wherein after transmitting and prior to printing the rendered object model, a simulation operation is performed on the rendered object model.

8. The bioassembly system according to claim 1, wherein after transmitting and prior to printing the rendered object model, at least one materials test print is conducted and information derived from the test print is applied to guide the printing and may be stored for future printing applications.

9. The bioassembly system according to claim 1, wherein the framed housing is operationally accessible to a user from multiple angles and provides at least one real-time observation access.

10. The bioassembly system according to claim 1, wherein the multi-axis robot comprises a six-axis robot.

11. The bioassembly system according to claim 1, wherein the material dispensing system comprises extrusion syringe dispensers adapted for direct-writing a biomaterial onto a substrate.

12. The bioassembly system according to claim 11, wherein dispensing from the material dispensing system may be effectuated at an angle oblique to a plane of a surface of a print substrate.

13. The bioassembly system according to claim 1, wherein the robotic arm effector component comprises one or more effectors selected from printing tools, staging and assembling tools, and sensors, and the system further comprises automatic tool exchange functionality for effectuating automated exchange of tools at the effector component as dictated by the print and/or assembly command.

14. The bioassembly system according to claim 13, wherein printing tools are selected from a gripper, a syringe barrel adapting holder and a dispenser, and wherein the staging and assembling tools are selected from picking, placing, and positioning tools, and wherein the sensors are selected from a laser displacement sensor and a photoelectric sensor.

15. The bioassembly system according to claim 14, wherein the robotic arm effector comprises a laser displacement sensor and the adjustable print stage comprises a leveling mechanism comprising a manual component enhanced by feedback from the laser displacement sensor.

16. The bioassembly system according to claim 15, wherein staging comprises picking and positioning a print substrate onto the print stage and the method comprises at least one step of staging and printing onto the print substrate.

17. The bioassembly system according to claim 16, wherein assembling comprises picking and positioning a first printed construct relative to a second construct, the second construct selected from a second printed construct and a provided construct.

18. The bioassembly system according to claim 15, wherein the print substrate comprises variable surface topography.

19. The bioassembly system according to claim 1, wherein the material dispensing system comprises multiple syringes, each syringe containing one material or bio-material, wherein dispensing from a syringe comprises dispensing one material or biomaterial at a time.

20. The bioassembly system according to claim 1, wherein the material storage unit comprises: at least one syringe barrel holder, each syringe barrel holder comprising multiple syringe barrels; at least one displacement sensor for ensuring correct seating of syringe barrels in the holder; and at least one needle detection sensor for detecting needle size and tip deflection.

21. The bioassembly system according to claim 1, wherein the robotic bioassembly workstation component comprises a framed housing comprising a multi-axis robot comprising a robotic arm having a robotic arm effector component, a robotic controller, a material storage unit, a material dispensing system, an adjustable print stage, and a user interface.

\* \* \* \* \*

UNITED STATES PATENT AND TRADEMARK OFFICE
CERTIFICATE OF CORRECTION

PATENT NO. : 9,910,935 B2
APPLICATION NO. : 14/511693
DATED : March 6, 2018
INVENTOR(S) : Michael Golway et al.

It is certified that error appears in the above-identified patent and that said Letters Patent is hereby corrected as shown below:

In the Claims

Column 25, Line 22-Column 26, approximately Lines 1-40:

Claim 9, replace "The bioassembly system according to claim 1, wherein the framed housing is operationally accessible to a user from multiple angles and provides at least one real-time observation access" with --The bioassembly system according to claim 1, wherein the robotic bioassembly workstation component comprises a framed housing comprising a multi-axis robot comprising a robotic arm having a robotic arm effector component, a robotic controller, a material storage unit, a material dispensing system, an adjustable print stage, and a user interface--.

Claim 10, replace "The bioassembly system according to claim 1, wherein the multi-axis robot comprises a six-axis robot" with --The bioassembly system according to claim 9, wherein the framed housing is operationally accessible to a user from multiple angles and provides at least one real-time observation access--.

Claim 11, replace "The bioassembly system according to claim 1, wherein the material dispensing system comprises extrusion syringe dispensers adapted for direct-writing a biomaterial onto a substrate" with --The bioassembly system according to claim 9, wherein the multi-axis robot comprises a six-axis robot--.

Claim 12, replace "The bioassembly system according to claim 11, wherein dispensing from the material dispensing system may be effectuated at an angle oblique to a plane of a surface of a print substrate" with --The bioassembly system according to claim 9, wherein the material dispensing system comprises extrusion syringe dispensers adapted for direct-writing a biomaterial onto a substrate--.

Claim 13, replace "The bioassembly system according to claim 1, wherein the robotic arm effector component comprises one or more effectors selected from printing tools, staging and assembling tools, and sensors, and the system further comprises automatic tool exchange functionality for effectuating Signed and Sealed this
Thirty-first Day of May, 2022

Katherine Kelly Vidal
*Director of the United States Patent and Trademark Office* automated exchange of tools at the effector component as dictated by the print and/or assembly command." with --The bioassembly system according to claim 12, wherein dispensing from the material dispensing system may be effectuated at an angle oblique to a plane of a surface of a print substrate--.

Claim 14, replace "The bioassembly system according to claim 13, wherein printing tools are selected from a gripper, a syringe barrel adapting holder and a dispenser, and wherein the staging and assembling tools are selected from picking, placing, and positioning tools, and wherein the sensors are selected from a laser displacement sensor and a photoelectric sensor" with --The bioassembly system according to claim 9, wherein the robotic arm effector component comprises one or more effectors selected from printing tools, staging and assembling tools, and sensors, and the system further comprises automatic tool exchange functionality for effectuating automated exchange of tools at the effector component as dictated by the print and/or assembly command--.

Claim 15, replace "The bioassembly system according to claim 14, wherein the robotic arm effector comprises a laser displacement sensor and the adjustable print stage comprises a leveling mechanism comprising a manual component enhanced by feedback from the laser displacement sensor" with --The bioassembly system according to claim 14, wherein printing tools are selected from a gripper, a syringe barrel adapting holder and a dispenser, and wherein the staging and assembling tools are selected from picking, placing, and positioning tools, and wherein the sensors are selected from a laser displacement sensor and a photoelectric sensor--.

Claim 16, replace "The bioassembly system according to claim 15, wherein staging comprises picking and positioning a print substrate onto the print stage and the method comprises at least one step of staging and printing onto the print substrate" with --The bioassembly system according to claim 15, wherein the robotic arm effector comprises a laser displacement sensor and the adjustable print stage comprises a leveling mechanism comprising a manual component enhanced by feedback from the laser displacement sensor--.

Claim 17, replace "The bioassembly system according to claim 16, wherein assembling comprises picking and positioning a first printed construct relative to a second construct, the second construct selected from a second printed construct and a provided construct" with --The bioassembly system according to claim 16, wherein staging comprises picking and positioning a print substrate onto the print stage and the method comprises at least one step of staging and printing onto the print substrate--.

Claim 18, replace "The bioassembly system according to claim 15, wherein the print substrate comprises variable surface topography" with --The bioassembly system according to claim 17, wherein assembling comprises picking and positioning a first printed construct relative to a second construct, the second construct selected from a second printed construct and a provided construct--.

Claim 19, replace "The bioassembly system according to claim 1, wherein the material dispensing system comprises multiple syringes, each syringe containing one material or bio-material, wherein dispensing from a syringe comprises dispensing one material or biomaterial at a time" with --The bioassembly system according to claim 16, wherein the print substrate comprises variable surface topography--.

Claim 20, replace "The bioassembly system according to claim 1, wherein the material storage unit comprises: at least one syringe barrel holder, each syringe barrel holder comprising multiple syringe barrels; at least one displacement sensor for ensuring correct seating of syringe barrels in the holder; and at least one needle detection sensor for detecting needle size and tip deflection" with --The bioassembly system according to claim 9, wherein the material dispensing system comprises multiple syringes, each syringe containing one material or bio-material, wherein dispensing from a syringe comprises dispensing one material or biomaterial at a time--.

Claim 21, replace "The bioassembly system according to claim 1, wherein the robotic bioassembly workstation component comprises a framed housing comprising a multi-axis robot comprising a robotic arm having a robotic arm effector component, a robotic controller, a material storage unit, a material dispensing system, an adjustable print stage, and a user interface" with --The bioassembly system according to claim 9, wherein the material storage unit comprises: at least one syringe barrel holder, each syringe barrel holder comprising multiple syringe barrels; at least one displacement sensor for ensuring correct seating of syringe barrels in the holder; and at least one needle detection sensor for detecting needle size and tip deflection--.